(12) United States Patent
Skerry et al.

(10) Patent No.: US 8,389,237 B2
(45) Date of Patent: Mar. 5, 2013

(54) ANTIBODIES AGAINST RAMP3

(75) Inventors: Timothy Michael Skerry, Sheffield (GB); Gareth Owain Richards, Sheffield (GB)

(73) Assignee: Medella Therapeutics Limited, Sheffield, South Yorkshire (GB)

( * ) Notice: Subject to any disclaimer, the term of this patent is extended or adjusted under 35 U.S.C. 154(b) by 108 days.

(21) Appl. No.: 12/597,269

(22) PCT Filed: Apr. 23, 2008

(86) PCT No.: PCT/GB2008/001454
§ 371 (c)(1),
(2), (4) Date: Oct. 23, 2009

(87) PCT Pub. No.: WO2008/132453
PCT Pub. Date: Nov. 6, 2008

(65) Prior Publication Data
US 2010/0111932 A1    May 6, 2010

(30) Foreign Application Priority Data

Apr. 25, 2007   (GB) .................................. 0708002.1

(51) Int. Cl.
*C12P 21/08* (2006.01)
(52) U.S. Cl. .................... 435/69.1; 435/320.1; 435/325; 536/23.5; 530/350; 530/387.1; 530/387.3; 530/388.22
(58) Field of Classification Search .................. 530/530, 530/387.1, 387.3, 388.22, 350; 536/23.5; 435/69.1, 320.1, 325
See application file for complete search history.

(56) References Cited

U.S. PATENT DOCUMENTS

2006/0099622 A1*   5/2006   Ni et al. ............................ 435/6

FOREIGN PATENT DOCUMENTS

| WO | 2004050834 A2 | 6/2004 |
| WO | 2007045927 A2 | 4/2007 |

OTHER PUBLICATIONS

Cottrel et al. (J. Comp. Neurol. Sep. 26, 2005; 490 (3): 239-55).*
Nowak et al. (Am. J. Physiol. Cell Physiol. Jun. 2002; 282 (6): C1322-31).*
Campbell (Monoclonal Antibody Technology, Laboratory Techniques in Biochemistry and Molecular Biology, 1984, Elsevier Science Publishers B.V.: Amsterdam, The Netherlands, vol. 13, pp. 1-32).*
Caldas et al. (Mol. Immunol. May 2003; 39 (15): 941-952).*
Chien et al. (Proc. Natl. Acad. Sci. USA. Jul. 1989; 86 (14): 5532-5536).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Gussow et al. (Methods in Enzymology. 1991; 203: 99-121).*
Mariuzza et al. (Annu. Rev. Biophys. Biophys. Chem. 1987; 16: 139-159).*
Rudikoff et al (Proc. Natl. Acad. Sci. USA. 1982; 79: 1979-1983).*
Keleg, Shereen et al., "Adrenomedullin is induced by hypoxia and enhances pancreatic cancer cell invasion," International Journal of Cancer, vol. 121, pp. 21-32 (2007).
"Ramp Antibodies," Internet Article, http://www.scbt.com/table.php?table=ramp, Santa Cruz Biotechnology, Inc., (2007).

* cited by examiner

*Primary Examiner* — Stephen Rawlings
(74) *Attorney, Agent, or Firm* — Speckman Law Group PLLC; Janet Sleath

(57) ABSTRACT

The present invention provides an isolated antibody capable of binding a receptor activity modifying protein (RAMP) of CRLR receptor which antibody is of IgG, IgA or IgM isotype.

17 Claims, 20 Drawing Sheets

(DNA)

ACTAGTCGACATGAGGG6CCCCTGCTCAGTTTT6TTGGGATCTTGTTGCTCTTGTTTCCAGGTACCAGA
TGTGACATCCAGATGACCCAGTCTCCATCCTCCTTATCTGCCTCTCTGGGAGAAAGAGTCAGTCTCAC
TTGTCGGGCAAGTCAGGACATTGGTAGTAACTTAAACTGGCTTCAGCAGGAACCAGATGGAACTATTA
AACGCCTGATCTACGCCACATCCAGTTTAGATTCTGGTGTCCCCAAAAGGTTCAGTGGCAGTAGGTCT
GGGTCAGATTATTCTCTCACCATCAGCAGCCTTGAGTCTGAAGATTTTGTAGACTATTACTGTCTACAA
TATGCTAGTTCTCCTCCGACGTTCGGTGGAGGCACCAAGCTGGAAATCAAACGGGCTGATGCTGCAC
CAACTGTATCCATCTTCCCACCATCCAGTAAGCTTGGG (Protein)

MVFGLSWVFLVALLRGVQCQVQLVESGGGVVQPGKSLRLSCAASGFTFSSYGMYWVRQAPGKGLEWVA
VISYDGSNKYYADSVKGRFTISRDNSKNTLYLQMNSLRAEDTAVYNCAKEMRYGSGRKAIKYYYGMDVWG
QGTTVTVSSASTKGPSVFPLA (b)

(DNA)

ACTAGTCGACATGAACTTCGGGTTCAGATTGGTTTTCCTAGCCCTCATTTTAAAAGGTGTCCAGTGTGA
AGTGCAGCTGGTGGAGTCTGGGGGAGGCTTAGTGAAGCCTGGAGGGTCCCTGAAACTCTCCTGTGCA
GCCTCTGGATTCACTTTCAGTAGTTATGCCATGTCTTGGGTTCGCCAGACTCCGGAGAAGAGGCTGGA
GTGGGTCGCAACCATTAGTAGTGGTGGTAGTTACACCTACTATCCAGACAGTGTGAAGGGTCGATTCA
CCATCTCCAGAGACAATGCCAAGAACACCCTGTACCTGCAAATGAGCAGTCTGAGGTCTGAGGACACG
GCCATGTATTACAGTGCAAGACATAGGTACGACGTGAAGTTTTTGGGCTACTGGGGCCAAGGCACCAC
TCTCACAGTCTCCTCAGAGAGTCAGTCCTTCCCAAATGTCTTCCCCCTCGTAAGCTTGGG (Protein)

LVDMNFGLRLVFLALILKGVQCEVQLVESGGGLVKPGGSLKLSCAASGFTFSSYAMSWVRQTPEKRLEWV
ATISSGGSYTYYPDSVKGRFTISRDNAKNTLYLQMSSLRSEDTAMYYSARHRYDVKFLGYWGQGTTLTVSS
ESQSFPNVFPLVSL (c)

(DNA)

AGGTGAAGCTGCAGGAGTCAGGGGCAGAGCTTGTGAGGTCAGGGGCCCCAGTCAAGTTGTCCTGCA
CAGCTTCTGGCTTCAACATTAAAGACTACTATATGCACTGGGTGAAGCAGAGGCCTGAACAGGGCCTG
GAGTGGATTGGATGGATTGATCCTGAGAATGGTGATACTGAATATGCCCCGAATTTCCAGGGCAAGGC
CACTATGACTGCAGACACATCCTCCAACACAGCCTACCTGCAGCTCAGCAGCCTGACATCTGAGGACA
CTGCCGTCTATTACTGTAATGCCCATGTTTTATTACTACGGGGAGTAGAGGATGCTATGGACTACTGG
GGCCAAGGGACCACGGTCACCGTCTCCTCA (Protein)

VKLQESGAELVRSGAPVKLSCTASGFNIKDYYMHWVKQRPEQGLEWIGWIDPENGDTEYAPNFQGKATM
TADTSSNTAYLQLSSLTSEDTAVYYCNAHVLLLRGVEDAMDYWGQGTTVTVSS (d)

(DNA)

ATGGACTTCGGGTTGAGCTGGGTTTTCCTTGTTGCTATTTTAAAAGGTGTCCAATGTGAGGTGCAGCT
GGTGGAGTCTGGGGGAGGCTTGGTACAGCCAGGGCGGTCCCTGAGACTCTCCTGTACAGCTTCTAGA
TTCACGTTTGCTGATTATGCTATCACCTGGGTCCGCCAGGCTCCAGGGAAGGGGCTGGAGTGGGTAG
GTTTCATTAGAAGCAAACCTTTTGGTGGACAGCAGCATACGCCGCGTCTGTGAAAGGCAGATTCACC
ATCTCAAGAGATGATTCCAAAAGCATCGCCTATCTGCAATTGAACCGCCTGAAAACCGAAGACACAGC
CGTGTATTACTGTAGTAGAGCCCCTTATCGAGTGACTACAGTCCCTCCTTGGACGTCTGGGGCCAAG
GGACCACGGTCACCGTCTCCTCAAGATCCGCCTCCACCAAGGGCCCATCCGTCTTCCCCCTGGCAC (Protein)

MDFGLSWVFLVAILKGVQCEVQLVESGGGLVQPGRSLRLSCTASRFTFADYAITWVRQAPGKGLEWVGFI
RSKPFGGTAAYAASVKGRFTISRDDSKSIAYLQLNRLKTEDTAVYYCSRAPLSSDYSPSLDVWGQGTTVTV
SSRSASTKGPSVFPLA

(DNA)

ATGAGGGCCCCTGCTCAGTTTTTTGGGATCTTGTTGCTCTTGTTTCCAGGTACCAGATGTGACATCCAG
ATGACCCAGTCTCCATCCTCCTTATCTGCCTCTCTGGGAGAAAGAGTCAGTCTCACTTGTCGGGCAAG
TCAGGACATTGGTAGTAACTTAAACTGGCTTCAGCAGGAACCAGATGGAACTATTAAACGCCTGATCTA
CGCCACATCCAGTTTAGATTCTGGTGTCCCCAAAAGGTTCAGTGGCAGTAGGTCTGGGTCAGATTATT
CTCTCACCATCAGCAGCCTTGAGTCTGAAGATTTTGTAGACTATTACTGTCTACAATATGCTAGTTCTCC
TCCGACGTTCGGTGGAGGCACCAAGCTGGAAATCAAACGGGCTGATGCTGCACCAACTGTATCCATCT
TCCCACCATCCAGT (Protein)

MRAPAQFFGILLLLFPGTRCDIQMTQSPSSLSASLGERVSLTCRASQDIGSNLNWLQQEPDGTIKRLIYATS
SLDSGVPKRFSGSRSGSDYSLTISSLESEDFVDYYCLQYASSPPTFGGGTKLEIKRADAAPTVSIFPPSSKL
G (b)

(DNA)

GACATCCAGATGACGCAGTCTCCAGCCTCCCTATCTGCATCTGTGGGAGAAACTGTCACCATCACATG
TCGAGCAAGTGAGAATATTTACAGTTATTTAGCATGGTATCAGCAGAAACAGGGAAAATCTCCTCAGCT
CCTGGTCTATAATGCAAAAACCTTAGCAGAAGGTGTGCCATCAAGGTTCAGTGGCAGTGGATCAGGCA
CACAGTTTTCTCTGAAGATCAACAGCCTGCAGCCTGAAGATTTTGGGAGTTATTACTGTCAACATCATT
ATGGTACTCCTCCGACGTTCGGTGGAGGCACCAAGCTGGAAATCAAACGG (Protein)

DIQMTQSPASLSASVGETVTITCRASENIYSYLAWYQQKQGKSPQLLVYNAKTLAEGVPSRFSGSGSGTQF
SLKINSLQPEDFGSYYCQHHYGTPPTFGGGTKLEIKR (c)

(DNA)

TTTTTTGAATTCCACCATGAAGTTGCCTGTTAGGCTGTTGGTGCTGATGTTCTGGATTCCTGCTTCCAG
CAGTGATGTTGTGATGACCCAAACTCCACTCTCCCTGCCTGTCAGTCTTGGAGATCAAGCCTCCATCT
CTTGCAGATCTAGTCAGAGCCTTGTACACAGTAATGGAAACACCTATTTACATTGGTACCTGCAGAAGC
CAGGCCAGTCTCCAAAGCTCCTGATCTACAAAGTTTCCAACCGATTTTCTGGGGTCCCAGACAGGTTC
AGTGGCAGTGGATCAGGGACAGATTTCACACTCAAGATCAGCAGAGTGGAGGCTGAGGATCTGGGAG
TTTATTTCTGCTCTCAAAGTACACATGTTCCATTCACGTTCGGCTCGGGGACAAAGTTGGAAATAAAC
GGGCTGATGCTGCACCAACTGTATCCATCTTCCCACCATCCAGTGAGCAGTTAACATCTGGAGGTGCC
TCAGTCGTGTGCTTCTTGAACAACTTCTACCCCAAAGA (Protein)

FLNSTMKLPVRLLVLMFWIPASSSDVVMTQTPLSLPVSLGDQASISCRSSQSLVHSNGNTYLHWYLQKPGQ
SPKLLIYKVSNRFSGVPDRFSGSGSGTDFTLKISRVEAEDLGVYFCSQSTHVPFTFGSGTKLEIKRADAAPT
VSIFPPSSEQLTSGGASVVCFLNNFYPK (d)

(DNA)

ATGGAGACAGACACACTCCTGCTATGGGTACTGCTGCTCTGGGTTCCAGGTTCCACTGGTGACATTGT
GCTGACACAGTCTCCTGCTTCCTTAGCTGTATCTCTGGGGCAGAGGGCCACCATCTCGTACAGGGCC
AGCAAAAGTGTCAGTACATCTGGCTATAGTTATATGCACTGGAACCAACAGAAACCAGGACAG8CCAC
CCAGACTCCTCATCTATCTTGTATCCAACCTAGAATCTGGGGTCCCTGCCAGGTTCAGTGGCAGTGGG
TCTGGGACAGACTTCACCCTCAACATCCATCCTGTGGAGGAGGATGCTGCAACCTATTACTGTCA
8GCACATTAGGGAGCTTACACGTTCGGAGGGGGGCACCAAGCTGGAAATCAAACGGAGATCTCGAAC
TGTGGCTGCACCATCTGTCT8TCATCTTCCCGCCATCTGATGAGCAGTTGAAATCTGGAACTGCCTCTG
TTGTGTGCCTGC (Protein)

METDTLLLWVLLLWVPGSTGDIVLTQSPASLAVSLGQRATISYRASKSVSTSGYSYMHWNQQKPGQPPRL
LIYLVSNLESGVPARFSGSGSGTDFTLNIHPVEEEDAATYYCQHIRELTRSEGGTKLEIKRRSRTVAAPSVFI
FPPSDEQLKSGTASVVCL

MVFGLSWVFLVALLRGVQCQVQLVESGGGVVQPGKSLRLSCAASGFTFSSYGMYWVRQAPGKGLEWVA
VISYDGSNKYYADSVKGRFTISRDNSKNTLYLQMNSLRAEDTAVYNCAKEMRYGSGRKAIKYYYGMDVWG
QGTTVTVSSASTKGPSVFPLA (ii)

MVFGLSWVFLVALLRGVQCQVQLVESGGGVVQPGKSLRLSCAASGFTFSSYGMYWVRQAPGKGLEWVA
VISYDGSNKYYADSVKGRFTISRDNSKNTLYLQMNSLRAEDTAVYNCAKEMRYGSGRKAIKYYYGMDVWG
QGTTVTVSPASTKGPSVFPLA

LVDMNFGFSLVFLALILKGVQCEVQLVESGGGLVKPGGSLKLSCAASGFTFSSYAMSWVRQTPEKRLEWV
ATISSGGSYTYYPDSVKGRFTISRDNAKNTLYLQMSSLRSEDTAMYYSARHRYDVKFLGYWGQGTTLTVSS
ESQSFPNVFPLVSL (ii)

LVDMNFGFRLVFLALILKGVQCEVQLVESGGGLVKPGGSLKLSCAASGFTFSSYAMSWVRQTPEKRLEWV
ATISSGGSYTYYPDSVKGRFTISRDNAKNTLYLQMSSLRSEDTAMYYSARHRYDVKFLGYWGQGTTLTVSS
ESQSFPNVFPLVSL (iii)

LVDMNFGFRLVFLALILKGVQCEVQLVESGGGLVKPGGSLKLSCAASGFTFSSYAMSWVRQTPEKRLEWV
ATISSGGSYTYYPDSVKGRFTISRDNAKNTLYLQMSSLRSEDTAMYYSARHRYDVKFLGYWGQGTTLTVSS
ESQSFPNVFPLVSL (iv)

LVDMNFGLRLVFLALILKGVQCEVQLVESGGGLVKPGGSLKLSCAASGFTFSSYAMSWVRQTPEKRLEWV
VTISSGGSYTYYPDSVKGRFTISRDNAKNTLYLQMSSLRSEDTAMYYSARHRYDVKFLGYWGQGTTLTVSS
ESQSFPNVFPLVSL (v)

LVDMNFGLRLVFLALILKGVQCEVQLVESGGGLVKPGGSLKLSCAASGFTFSSYAMSWVRQTPEKRLEWV
ATISSGGSYTYYPDSVKGRFTISRDNAKNTLYLQMSSLRSEDTAMYYSARHRYDVKFLGYWGQGTTLTVSS
ESQSFPNVFPLVSL (vi)

LVDMNFGLSLVFLALILKGVQCEVQLVESGGGLVKPGGSLKLSCAASGFTFSSYAMSWVRQTPEKRLEWV
ATISSGGSYTYYPDSVKGRFTISRDNAKNTLYLQMSSLRSEDTAMYYSARHRYDVKFLGYWGQGTTLTVSS
ESQSFPNVFPLVSL

Figure 5

(i)
VKLQESGAELVRSGAPVELSCTASGFNIKDYYMHWVKQRPEQGLEWIGWIDPENGDTEYAPNFQGKATM
TADTSSNTAYLQLSSLTSEDTAVYYCNAHVLLLRGVEDAMDYWGQGTTVPSP (ii)
GQAQESGAELVRSGAPVKLSCTASGFNIKDYYMHWVKQRPEQGLEWIGWIDPENGDTEYAPNFQGKATM
TADTSSNTAYLQLSSLTSEDTAVYYCNAHVLLLRGVEDAMDYWGQGTTVTVSS (iii)
VKLQESGAGLVRSGAPVKLSCTASGFNIKDYYMHWVKQRPEQGLEWIGWIDPENGDTEYAPNFQGKATM
TADTSSNTAYLQLSSLTSEDTAVYYCNAHVLLLRGVEDAMDYWGQGTTVTSP (iv)
VKLQESGAELVRSGAPVKLSCTASGFNIKDYYMHWVKQRPEQGLEWIGWIDPENGDTEYAPNFQGKATM
TADTSSNTAYLQLSSLTSEDTAVYYCNAHVLLLRGVEDAMDYWGQGTTVTVSS (v)
VKLQESRAELVRSGAPVKLSCTASGFNIKDYYMHWVKQRPEQGLEWIGWIDPENGDTEYAPNFQGKATMT
ADTSSNTAYLQLSSLTSEDTAVYYCNAHVLLLRGVEDAMDYWGQGTTVTSP (vi)
VQLQESGAELVRSGAPVKLSCTASGFNIKDYYMHWVKQRPEQGLEWIGWIDPENGDTEYAPNFQGKATM
TADTSSNTAYLQLSSLTSEDTAVYYCNAHVLLLRGVEDAMDYWGQGTTVTVSS (vii)
VKLQESGAELVRSGAPVKLSCTASGFNIKDYYMHWVKQRPEQGLEWIGWIDPENGDTEYAPNFQGKATM
TADTSSNTAYLQLSSLTSEDTAVYYCNAHVLLLRGVEDAMDYWGQGTTVTVSS

Figure 6

(i)
MDFGLSWVFLVAILKGVQCEVQLVESGGGLVPPGRSLRLSCTASRFTFADYAITWVRQAPGKGLEWVGFI
RSKPFGGTAAYAASVKGRFTISRDDSKSIAYLQLNRLKTEDTAVYYCSRAPLSSDYSPSLDVWGQGTTVTV
SSRSASTKGPSVFPLA (ii)
MDFGLSWVFLVAILKGVQCEVQLVESGGGLVQPGRSLRLSCTASRFTFADYAITWVRQAPGKGLEWVGFI
RSKPFGGTAAYAASVKGRFTISRDDSKSIAYLQLNRLKTEDTAVYYCSRAPLSSDYSPSLDVWGQGTTVTV
SSRSASTKGPSVFPLA (iii)
MDFGLSWVFLVAILKGVQCEVQLVESGGGLVQPGRSLRLSCTASRFTFADYAITWVRQAPGKGLEWVGFI
RSKPFGGTAAYAXSVKGRFTISRDDSKSIAYLQLNRLKTEDTAVYYCSRAPLSSDYSPSLDVWGQGTTVTV
SSRSASTKGPSVFPLA (iv)
MDFGLSLVFLVAILKGVQCEVQLVESGGGLVQPGRSLRLSCTASRFTFADYAITWVRQAPGKGLEWVGFIR
SKPFGGTAAYAASVKGRFTISRDDSKSIAYLQLNRLKTEDTAVYYCSRAPLSSDYSPSLDVWGQGTTVTVS
SRSASTKGPSVFPLA (v)
MDFGLSWVFLVAILKGVQCEVQLVESGGGLVQPGRSLGLSCTASRFTFADYAITWVRQAPGKGLEWVGFI
RSKPFGGTAAYAASVKGRFTISRDDSKSIAYLQLNRLKTEDTAVYYCSRAPLSSDYSPSLDVWGQGTTVTV
SSRSASTKGP

Figure 7

(i)
LVDMRAPAQFFGILLLLFPGTRCDIQMTQSPSSLSASLGERVSLTCRASQDIGSNLNWLQQEPDGTIKRLIY
ATSSLDSGVPKRFSGSRSGSDYSLTISSLESEDFVDYYCLQYASSPPTFGGGTKLEIKRADAAPTVSIFPPS
SKLG (ii)
LVDMRAPAQIFGILLLLFPGTRCDIQMTQSPSSLSASLGERVSLTCRASQDIGSNLNWLQQEPDGTIKRLIYA
TSSLDSGVPKRFSGSRSGSDYSLTISSLESEDFVDYYCLQYASSPPTFGGGTKLEIKRADAAPTVSIFPPSS
KLG (iii)
LVDMRAPAQFLGILLLLFPGTRCDIQMTQSPSSLSASLGERVSLTCRASQDIGSNLNWLQQEPDRTIKRLIYA
TSSSDSGVPKRFSGSRSGSDYSLTISSLESEDSVDYYCLQYASSPPTFGGGTKLEIKRADAAPTVSIFPPSS
KLG (iv)
LVDMRTPAQFFGILLLLFPGTRCDIQMTQSPSSLSASLGERVSLTCRTSQDIGSNLNWLQQEPDGTIKRLIYA
TSSLDSGVPKRFSGSRSGSDYSLTISSLESEDFVDYYCLQYASSPPTFGGGTKLEIKRADAAPTVSIFPPSS
KLG (v)
TSRMVSTPQFLGFLLLLFPGTRCDIQMTQSPSSLSASLGERVSLTCRASQDIGSNLNWLQQEPDGTIKRLIY
ATSSLDSGVPKRFSGSRSGSDYSLTISSLESEDFVDYYCLQYASSPPTFGGGTKLEIKRADAAPTVSIFPPS
SKLG

Figure 8

(i)
DIQMTQSPASLSASVGETVTITCRASENIYSYLAWYQQKQGKSPQLLVYNAKTLAEGVPSRFSGSGSGTQF
SLKINSLQPEDFGSYYCQHHYGTPPTFGGGTKLEIKR (ii)
DIQMTQSPASLSASVGETVTITCRASENIYSYLAWYQQKQGKSPQLLVYNAKTLAEGVPSRFSGSGSGTQF
SLKINSLQPEDFGSYYCQHRYGTPPTFGGGTKLIKR (iii)
HQMTQSPASLSASVGETVTITCRASENIYSYLAWYQQKQGKSPQLLVYNAKTLAEGVPSRFSGSGSGTQF
SLKINSLQPEDFGSYYCQHHYGTPPTFGGGTKLEIKR (iv)
DIQMTQSPASLSASVGETVTITCRASENIYSYLAWYQQKQGKSPQLLVYNAKTLAEGVPSRFSGSGSGTQF
SLKINSLQPEDFGSYYCQHHYGTPPTFGGGTKLEIK (v)
DIQMTQSPASLSASVGETVTITCRASENIYSYLAWYQQKQGKSPQLLVYNAKTLAEGVPSRFSGSGSGTQF
SLKINSLQPEDFGSYYCQHHYGTPPTFGGGTKLEIKR

Figure 9

(i)
FLNSTMKLPVRLLVLMFWIPASSSDVVMTQTPLSLPVSLGDQASISCRSSQSLVHSNGNTYLHWYLQKPGQ
SPKLLIYKVSNRFSGVPDRFSGSGSGTDFTLKISRVEAEDLGVYFCSQSTHVPFTFGSGTRLEIKRADAAPT
VSIFPPSSEQLTSGGASVVCFLNNFYPK (ii)
STMKLPVRLLVLMFWIPASSSDVVMTQTPLSLPVSLGDQASISCRSSQSLVHSNGNTYLHWYLQKPGQSPK
LLIYKVSNRFSGVPDRFSGSGSGTDFTLKISRVEAEDLGVYFCSQSTHVPFTFGSGTKLEIKRANAAPTVSIF
PPSSEQLTSGGASVVCFLNNFYPK (iii)
FLNSTMKLPVRLLVLMFWIPASSSDVVMTQTPLSLPVSLGDQASISCRSSQSLVHSNGNTYLHWYLQKPGQ
SPKLLIYKVSNRFSGVPDRFSGSGSGTDFTLKISRVEAEDLGVYFCSQSTHVPFTFGSGTKLEIKRADAAPT
VSIFPPSSEQLTSGGASVMCFLNNFYPR (iv)
FLNSTMKLPVRLLVLMFWIPASSSDVVMTQTPLPLPVSLGDQASISCRSSQSLVHSNGNTYLHWYLQKPGQ
SPKLLIYKVSNRFSGVPDRFSGSGSGTDFTLKISRVEAEDLGVYFCSQSTHVPFTFGSGTKLEIKRADAAPT
VSIFPPSSEQLTSGGASVVCFLNNFYPK (v)
NSTMKLPVRLLVLMFWIPASSSDVVMTQTPLSLPVSLGDQASISCRSSQSLVHSNGNTYLHWYLQKPGQS
PKLLIYKVSNRFSGVPDRFSGSGSGTDFTLKISRVEAEDLGVYFCSQSTHVPFTFGSGTKLEIKRADAAPTV
SIFPPSSEQLTSGGASVVCFLNNFYPK

Figure 10

(i)
METDTLLLWVLLLWVPGSTGDIVLTQSPASLAVSLGQRATISYRASKSVSTSGYSYMHWNQQKPGHPPRLL
IYLVSNLESGVPARFSGSGSGTDFTLNIHPVEEEDAATYYCRHIRELTRSEGGTKLEIKRRSRTVAAPSVFIF
PPSDEQLKSGTASVVCL (ii)
METDTLLLWVLLLWVPGSTGDIVLTQSPASLAVSLGQRATISYRASKSVSTSGYSYMHWNQQKPGQPPRL
LIYLVSNLESGVPARFSGSGSGTDFTLNIHPVEEEDAATYYCQHIRELTRSEGGTKLEIKRRSRTVAAPSVLIF
PPSDEQLKSGTASVVCL (iii)
METDTLLLWVLLLWVPGSTGDIVLTQSPASLAVSLGQRATISYRASKSVSTSGYSYMHWNQQKPGQPPRL
LIYLVSNLESGVPARFSGSGSGTDFTLNIHPVEEEDAATYYCQHIRELTRSEGGTKLEIKRRSRTVAAPSVFI
FPPSDEQLKSGTASVVCL (iv)
METDTLLLWVLLLWVPGSTGDIVLTQSPASLAVSLGQRATISYRASKSVSTSGYSYMHWNQQKPGQPPRL
LIYLVSNLESGVPARFSGSGSGTDFTLNIHPVEEEDAATYYCQHIRELTRSEGGTKLEIKRRSRTVAAPSVFI
FPPSDEQLKSGTASVVCL (v)
METDTLLLWVLLLWVPGSTGDIVLTQSPASLAVSLGQRATISYRASKSVSTSGYSYMHWNQQKPGQPPRL
LIYLVSNLESGVPARFSGSGSGTDFTLNIHPVEEEDAATYYCQHIRELTRSEGGTKLEIKRRSRTVAAPSVFI
FPPSDEQLKSGTASVVCL

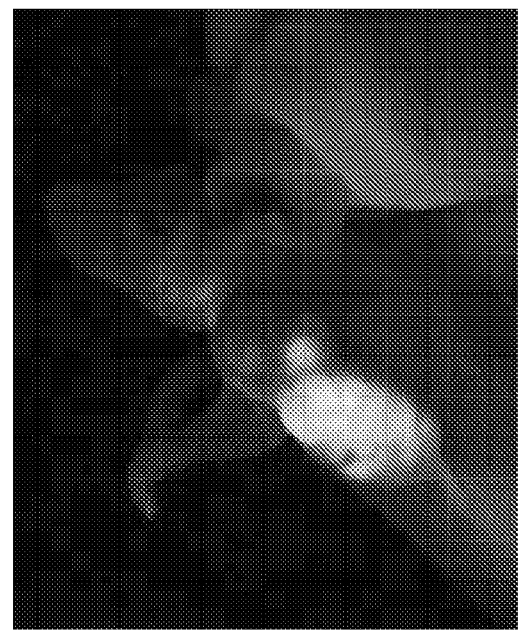
PBS Control
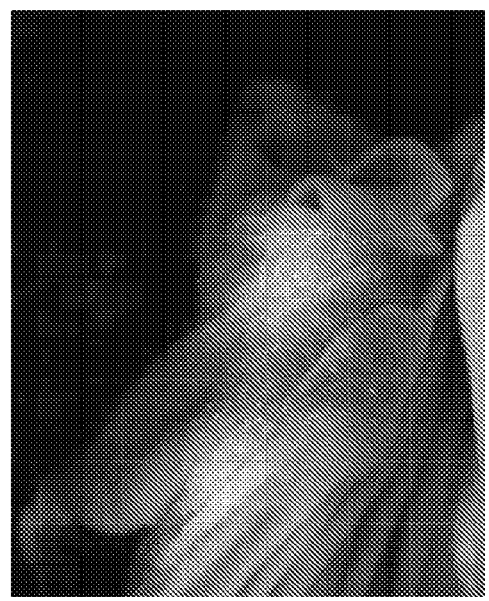
Treatment Group
Figure 26

Isotype Group

Control  JF2 Treatment

ANTIBODIES AGAINST RAMP3

REFERENCE TO RELATED APPLICATIONS

This application is the US national phase entry of International Patent Application No. PCT/GB2008/001454, filed Apr. 23, 2008, which claims priority to GB Patent Application No. 0708002.1, filed Apr. 25, 2007.

FIELD OF THE INVENTION

The present invention relates to antibodies and fragments thereof which bind to a receptor activity modifying protein (RAMP) associated with the calcitonin receptor like receptor.

BACKGROUND TO THE INVENTION

The calcitonin family of peptides act through G-protein coupled membrane receptors (GPCRs). The gene for calcitonin receptors has been cloned. It is homologous to GPCRs in family "B" which typically recognize regulatory peptides (secretin, glucagons, VIP). A homolog of the calcitonin receptor, the Calcitonin Receptor Like Receptor (CRLR, also known as CL) has been identified (human 461 aa; rat/mouse 463 aa) and has 55% homology with calcitonin receptor (Njuki et al., *Clin. Sci.* 85, 385-388 (1993); Chang et al., *Neuron* 11, 1187-1195 (1993); Fluhmann et al., *Biochem. Biophys. Res. Comun.* 206, 341-347 (1995); Kapas et al., *J. Biol. Chem.* 270, 25344-25347 (1995)).

Alone, the CRLR is unable to transduce a signal in response to adrenomedullin (AM), as the presence of a RAMP (calcitonin Receptor Activity Modifying Protein) is needed to induce ligand specificity, binding and activation of the CRLR. The RAMPs are a family of small intrinsic membrane proteins, with a predicted sizes of 14,000-17,0000 Kd. RAMPs consists of approximately 120 amino acids with a large extra-cellular domains of around 100 amino acids; a single membrane spanning domain and a short intra-cellular region of approximately 10 amino acids.

It has been shown that CRLR can function as either a CGRP receptor or an AM receptor, depending upon which members of the RAMP family, RAMPs1-3, are expressed. The three members of the RAMP family, RAMP1, 2 and 3, engender different ligand specificities of the CRLR so that:

RAMP1+CRLR=CGRP receptor

RAMP2+CRLR=AM receptor

RAMP3+CRLR=AM receptor

The sequences of RAMP 1, 2 and 3 are available as follows:
RAMP 1—GenBank™ Accession No. NM_005835
RAMP 2—GenBank™ Accession No. NM_005854; UniGene™ ID Hs. 155106
RAMP 3—GenBank™ Accession No. NM_005856; UniGene™ ID Hs. 25691

Polyclonal antibodies which bind to RAMP2 and are useful in the treatment of cancer are disclosed in WO2004/050834. The antibodies were raised to a region of the extracellular domain of RAMP2 believed to be critical for CRLR binding to RAMP2.

Because of the high potential utility such anti-RAMP antibodies could have in therapy and diagnosis there is a need for further anti-RAMP antibodies.

The present inventors have isolated and characterised further anti-RAMP antibodies. These antibodies have, inter alia, been shown to inhibit cancer cell proliferation and are useful in the prevention of cancer.

SUMMARY OF THE INVENTION

According to a first aspect of the present invention, there is provided an isolated antibody capable of binding a receptor activity modifying protein (RAMP) of CRLR receptor which antibody is of IgG, IgA or IgM isotype.

In one embodiment the antibody of the first aspect of the invention is of IgG isotype. The antibody may be of the subclass IgG1, IgG2, IgG3 or IgG4. Preferably the antibody is of IgG1 isotype.

In another embodiment the antibody of the first aspect of the invention is of IgA isotype. The antibody may be of the subclass IgA1 or IgA2.

In a further embodiment the antibody of the first aspect of the invention is of IgM isotype.

The antibody of the first aspect of the invention may be a monomeric, dimeric, trimeric, tetrameric or pentameric polypeptide.

The antibody may be capable of binding RAMP1, RAMP2 or RAMP3. Preferably the antibodies of the invention are capable of binding to RAMP3.

The antibody of the invention may be a RAMP antagonist or agonist or potentiator of the activity of natural or artificial ligands to the receptor.

The antibody of the invention may function as a RAMP antagonist. The data disclosed herein may indicate that the antibody may inhibit either the interaction between RAMP and CRLR on the one hand or inhibit the interaction between a RAMP/CRLR associated complex and a ligand such as adrenomedullin. In one embodiment the antibody is an anti-RAMP3 antibody of IgM isotype and is a RAMP antagonist. In further embodiment the antibody is an anti-RAMP3 antibody of IgG1 isotype and is a RAMP antagonist.

In one embodiment, the antibody of the invention functions as a RAMP agonist. The data disclosed herein may indicate that the antibody may In one embodiment the antibody is an anti-RAMP3 antibody of IgG1 isotype and is a RAMP agonist or RAMP potentiator of AM action.

A second aspect of the invention provides an isolated antibody capable of binding a receptor activity modifying protein (RAMP) of CRLR receptor which antibody comprises a binding domain selected from the group consisting of:
i) a binding domain comprising an amino acid sequence encoded by a nucleic acid molecule consisting of a nucleic acid sequence as represented by a sequence shown in FIG. 1*a* (SEQ ID NO: 1);
ii) a binding domain comprising an amino acid sequence encoded by a nucleic acid molecule consisting of a nucleic acid sequence as represented by a sequence shown in FIG. 1*b* (SEQ ID NO: 3);
iii) a binding domain comprising an amino acid sequence encoded by a nucleic acid molecule consisting of a nucleic acid sequence as represented by a sequence shown in FIG. 1*c* (SEQ ID NO: 5);
iv) a binding domain comprising an amino acid sequence encoded by a nucleic acid molecule consisting of a nucleic acid sequence as represented by a sequence shown in FIG. 1*d* (SEQ ID NO: 7);
v) a binding domain comprising an amino acid sequence encoded by a nucleic acid molecule which hybridises to a nucleic acid molecule as defined in (i), (ii), (iii) or (iv) above;
vi) a binding domain comprising an amino acid sequence encoded by a nucleic acid which is degenerate as a result of the genetic code to the nucleic acid sequence defined in (i), (ii), (iii), (iv) or (v).

In a third aspect, the invention provides an isolated antibody capable of binding a receptor activity modifying protein (RAMP) of CRLR receptor which antibody comprises a binding domain selected from the group consisting of:

i) a binding domain comprising an amino acid sequence encoded by a nucleic acid molecule consisting of a nucleic acid sequence as represented by a sequence shown in FIG. 2a (SEQ ID NO: 9);

ii) a binding domain comprising an amino acid sequence encoded by a nucleic acid molecule consisting of a nucleic acid sequence as represented by a sequence shown in FIG. 2b (SEQ ID NO: 11);

iii) a binding domain comprising an amino acid sequence encoded by a nucleic acid molecule consisting of a nucleic acid sequence as represented by a sequence shown in FIG. 2c (SEQ ID NO: 13);

iv) a binding domain comprising an amino acid sequence encoded by a nucleic acid molecule consisting of a nucleic acid sequence as represented by a sequence shown in FIG. 2d (SEQ ID NO: 15);

v) a binding domain comprising an amino acid sequence encoded by a nucleic acid molecule which hybridises to a nucleic acid molecule as defined in (i), (ii), (iii) or (iv) above; and vi) a binding domain comprising an amino acid sequence encoded by a nucleic acid which is degenerate as a result of the genetic code to the nucleic acid sequence defined in (i), (ii), (iii), (iv) or (v).

In a preferred aspect of the invention there is provided an isolated antibody capable of binding a receptor activity modifying protein of CRLR which antibody comprises one or both of the following binding domains:

i) a binding domain comprising an amino acid sequence encoded by a nucleic acid molecule consisting of a nucleic acid sequence as represented by a sequence shown in FIG. 1a (SEQ ID NO: 1); and/or ii) a binding domain comprising an amino acid sequence encoded by a nucleic acid molecule consisting of a nucleic acid sequence as represented by a sequence shown in FIG. 2a (SEQ ID NO: 9).

In a further preferred aspect of the invention there is provided an isolated antibody capable of binding a receptor activity modifying protein of CRLR which antibody comprises one or both of the following binding domains:

i) a binding domain comprising an amino acid sequence encoded by a nucleic acid molecule consisting of a nucleic acid sequence as represented by a sequence shown in FIG. 1b (SEQ ID NO: 3); and/or ii) a binding domain comprising an amino acid sequence encoded by a nucleic acid molecule consisting of a nucleic acid sequence as represented by a sequence shown in FIG. 2b (SEQ ID NO: 11).

The nucleic acid molecule may anneal under stringent hybridisation conditions to the nucleic acid sequence shown in FIG. 1 a to d or 2 a to d (SEQ ID NO: 1, 3, 5, 7, 9, 11, 13 and 15) or to its complementary strand. Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequences of the nucleic acid is known. For example, hybridisation conditions can be determined by the GC content of the nucleic acid subject to hybridisation. Please see Sambrook et al (1989) Molecular Cloning; A Laboratory Approach. A common formula for calculating the stringency conditions required to achieve hybridisation between nucleic acid molecules of a specified homology is:

$$T_m = 81.5° C. + 16.6 \log[Na^+] + 0.41[\% G+C] - 0.63$$
(% formamide).

A further aspect of the invention provides an isolated antibody capable of binding a receptor activity modifying protein (RAMP) of CRLR receptor which antibody comprises a binding domain selected from the group consisting of:

i) a binding domain comprising an amino acid sequence substantially as represented by a sequence shown in FIG. 1a (SEQ ID NO: 2);

ii) a binding domain comprising an amino acid sequence substantially as represented by a sequence shown in FIG. 1b (SEQ ID NO: 4);

iii) a binding domain comprising an amino acid sequence substantially as represented by a sequence shown in FIG. 1c (SEQ ID NO: 6); and iv) a binding domain comprising an amino acid sequence substantially as represented by a sequence shown in FIG. 1d (SEQ ID NO: 8).

In a further aspect, the invention provides an isolated antibody capable of binding a receptor activity modifying protein (RAMP) of CRLR receptor which antibody comprises a binding domain selected from the group consisting of:

i) a binding domain comprising an amino acid sequence substantially as represented by a sequence shown in FIG. 2a (SEQ ID NO: 10);

ii) a binding domain comprising an amino acid sequence substantially as represented by a sequence shown in FIG. 2b (SEQ ID NO: 12);

iii) a binding domain comprising an amino acid sequence substantially as represented by a sequence shown in FIG. 2c (SEQ ID NO: 14); and iv) a binding domain comprising an amino acid sequence substantially as represented by a sequence shown in FIG. 2d (SEQ ID NO: 16).

In a preferred aspect of the invention there is provided an isolated antibody capable of binding a receptor activity modifying protein of CRLR which antibody comprises one or both of the following binding domains:

i) a binding domain comprising an amino acid sequence substantially as represented by a sequence shown in FIG. 1a (SEQ ID NO: 2); and/or ii) a binding domain comprising an amino acid sequence substantially as represented by a sequence shown in FIG. 2a (SEQ ID NO: 10).

In a preferred aspect of the invention there is provided an isolated antibody capable of binding a receptor activity modifying protein of CRLR which antibody comprises one or both of the following binding domains:

i) a binding domain comprising an amino acid sequence substantially as represented by a sequence shown in FIG. 1b (SEQ ID NO: 4); and/or ii) a binding domain comprising an amino acid sequence substantially as represented by a sequence shown in FIG. 2b (SEQ ID NO: 12).

In one embodiment the antibody of the invention comprises a binding domain comprising an amino acid sequence substantially as set out in an amino acid sequence selected from those represented in FIG. 3 (SEQ ID NO: 17 and 18).

In one embodiment the antibody of the invention comprises a binding domain comprising an amino acid sequence substantially as set out in an amino acid sequence selected from those represented in FIG. 4 (SEQ ID NO: 19-24).

In one embodiment the antibody of the invention comprises a binding domain comprising an amino acid sequence substantially as set out in an amino acid sequence selected from those represented in FIG. 5 (SEQ ID NO: 25-31).

In one embodiment the antibody of the invention comprises a binding domain comprising an amino acid sequence substantially as set out in an amino acid sequence selected from those represented in FIG. 6 (SEQ ID NO: 32-36).

In one embodiment the antibody of the invention comprises a binding domain comprising an amino acid sequence substantially as set out in the amino acid sequence selected from those represented in FIG. 7 (SEQ ID NO: 37-41).

In one embodiment the antibody of the invention comprises a binding domain comprising an amino acid sequence substantially as set out in the amino acid sequence selected from those represented in FIG. 8 (SEQ ID NO: 42-46).

In one embodiment the antibody of the invention comprises a binding domain comprising an amino acid sequence substantially as set out in the amino acid sequence selected from those represented in FIG. 9 (SEQ ID NO: 47-51).

In one embodiment the antibody of the invention comprises a binding domain comprising an amino acid sequence substantially as set out in the amino acid sequence selected from those represented in FIG. 10 (SEQ ID NO: 52-56).

Antibodies which comprise a plurality of binding domains of the same or different sequence, or combinations thereof, are included within the present invention. The or each polypeptide may be carried by a human antibody framework. For example, one or more binding regions may be substituted for the CDRs of a whole human antibody or of the variable region thereof.

In a fourth aspect, the invention provides an antibody which comprises an antibody of the second aspect in combination or association with an antibody of the third aspect. Such an antibody may be in the form of a Fv, (Fab')2, or scFV antibody fragment.

Antibodies of the invention may carry a detectable or functional label.

In further aspects, the invention provides an isolated nucleic acid which comprises a sequence encoding an antibody of the first, second, third or fourth aspects of the invention, and methods of preparing antibodies of the invention which comprise expressing said nucleic acids under conditions to bring about expression of said antibody, and recovering the antibody.

Antibodies according to the invention may be used in a method of treatment, prevention or diagnosis of the human or animal body, such as a method of treatment of a proliferative disorder such as a tumour in a patient (preferably human) which comprises administering to said patient an effective amount of an antibody of the invention. The invention also provides an antibody of the present invention for use in medicine, as well as the use of an antibody of the present invention in the manufacture of a medicament for the diagnosis or treatment of a proliferative disorder such as a tumour.

Antibodies according to the invention may also be used in a method of treatment or prevention of an inflammatory disorder in a patient (preferably human) which comprises administering to said patient an effective amount of an antibody of the invention. The invention also provides the use of an antibody of the present invention in the manufacture of a medicament for the treatment of an inflammatory disorder.

The term "antibody" as used herein refers to immunoglobulin molecules and immunologically active portions of immunoglobulin molecules, i.e. molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced.

Examples of antibodies are fragments which comprise an antigen binding domain such as Fab, scFv, Fv, dAb, Fd; and diabodies.

Antibodies may be polyclonal or monoclonal. Preferably the antibody is a monoclonal antibody may be referred to herein as "mab".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any antibody or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539. It has been shown that fragments of a whole antibody can perform the function of binding antigens. Examples of binding fragments are (i) the Fab fragment consisting of VL, VH, CL and CHI domains; (ii) the Fd fragment consisting of the VH and CHI domains; (iii) the Fv fragment consisting of the VL and VH domains of a single antibody; (iv) the dAb fragment (Ward, E. S. et al., Nature 341: 544-546 (1989)) which consists of a VH domain; (v) isolated CDR regions; (vi) F(ab')$_2$ a bivalent fragment comprising two linked Fab fragments (vii) single chain Fv molecules (scFv), wherein a VH domain and a VL domain are linked by a peptide linker which allows the two domains to associate to form an antigen binding site (Bird et al., Science 242: 423-426 (1988); Huston et al., PNAS USA 85: 5879-5883 (1988)); (viii) bispecific single chain Fv dimmers (PCT/US92/09965) and (ix) "diabodies", multivalent or multispecific fragments constructed by gene fusion (WO94/13804; P. Hollinger et al., Proc. Natl. Acad. Sci. USA 90: 6444-6448 (1993)).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associated with each other to form an antigen binding site: antigen binding sites are formed by the association of the first domain of one polypeptide within the multimer with the second domain of another polypeptide within the multimer (WO94/13804).

The antibodies of the invention may be multispecific antibodies having specificity for at least two different antigens. While such a molecule is generally binds to two antigens (i.e., bispecific antibody), the term "multispecific antibody" in the present invention encompasses an antibody having specificity for two or more (such as three) antigens. The multispecific antibody can be a full length antibody or a fragment of such an antibody (e.g. F(ab')2 bispecific antibody). Where bispecific antibodies are to be used, these may be conventional bispecific antibodies, which can be manufactured in a variety of ways (Hollinger & Winter, Current Opinion Biotechnol. 4: 446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10: 3655-3659 (1991). The bispecific antibody also include a heteroconjugate antibody in which one antibody is coupled to avidin and the other is coupled to biotin or the like (U.S. Pat. No. 4,676,980, WO 91/00360, WO 92/200373, and EP 03089). A cross-linking agent to be used in the production of such a heteroconjugate antibody is well known, and is disclosed in, for instance, U.S. Pat. No. 4,676,980.

Bispecific diabodies, as opposed to bispecific whole antibodies, may also be useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

An "antigen binding domain" or "binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

"Isolated" refers to the state in which antibodies of the invention or nucleic acid encoding such antibodies will preferably be, in accordance with the present invention. Antibodies and nucleic acid will generally be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Antibodies and nucleic acid may be formulated with diluents or adjuvants and still for practical purposes be isolated—for example, the antibodies will normally be mixed with gelatin or other carriers if used to coat microtitre plates for use in immunoassays, or will be mixed with pharmaceutically acceptable carriers or diluents when used in diagnosis or therapy. Antibodies may be glycosylated, either naturally or by systems of heterologous eukaryotic cells, or they may be (for example if produced by expression in a prokaryotic cell) unglycosylated.

By "substantially as represented" it is meant that the amino acid sequence of the binding domain will be either identical or highly homologous to the amino acid sequence represented in the amino acid sequence shown in FIG. 1*a* to *d* (SEQ ID NO: 2, 4, 6, and 8), FIG. 2*a* to *d* (SEQ ID NO: 10, 12, 14 and 16) or FIGS. 3 to 10 (SEQ ID NO: 17-56).

By "highly homologous" it is contemplated that the amino acid sequence have at least 70% identity to the amino acid sequence represented in FIG. 1*a* to *d* (SEQ ID NO: 2, 4, 6, and 8), FIG. 2*a* to *d* (SEQ ID NO: 10, 12, 14 and 16) or FIGS. 3 to 10 (SEQ ID NO: 17-56). Preferably the amino acid sequence will have at least 80% identity, more preferably 80% identity to and more preferably at least 90% identity to and still more preferably at least 95% identity for example 98% identity to the amino acid sequence represented in FIG. 1*a* to *d* (SEQ ID NO: 2, 4, 6, and 8), FIG. 2*a* to *d* (SEQ ID NO: 10, 12, 14 and 16) or FIGS. 3 to 10 (SEQ ID NO: 17-56).

As used herein, "treatment" includes any regime that can benefit a human or non-human animal, preferably mammal. Mammals, birds and other animals may be treated including dogs, cats and livestock, such as horses, cattle and sheep, The treatment may be in respect of an existing condition or may be prophylactic (preventative treatment).

As used herein, a "tumour" is an abnormal growth of tissue. It may be localised (benign) or invade nearby tissues (malignant) or distant tissues (metastatic). Tumours include neoplastic growths which cause cancer and include oesophageal, colorectal, gastric, breast and endometrial tumours, as well as cancerous tissues or cell lines including, but not limited to, leukaemic cells. As used herein, "tumour" also includes within its scope endometriosis. Examples of tumours that may be treated in accordance with the invention include tumours of the skin, lung, mediastinum, pericardium, prostate, breast, colon & rectum, liver, pancreas, brain, intracranial structures, eye, testicle, ovary, uterus, cervix, kidney, thyroid, bladder, gastrointestinal tract, haematological tissue, bone, joints or colon.

As used herein, an "inflammatory disorder" includes disorders selected from the group consisting of atherosclerosis, rheumatoid arthritis, osteoarthritis, gout, lupus erythematosus, scleroderma, Sjorgen's syndrome, poly- and dermatomyositis, vasculitis, tendonitis, synovitis, bacterial endocarditis, osteomyelitis, psoriasis, pneumonia, fibrosing alveolitis, chronic bronchitis, bronchiectasis, emphysema, silicosis, pneumoconiosis, tuberculosis, ulcerative colitis, Crohn's disease, chronic inflammatory demyelinating polyradiculoneuropathy, chronic inflammatory demyelinating polyneuropathy, multiple sclerosis, Guillan-Barre Syndrome and myasthemia gravis, mastitis, laminitis, laryngitis, chronic cholecystitis, Hashimoto's thyroiditis, carpal tunnel syndrome and inflammatory breast disease. In an embodiment, the inflammatory disorder may be the result of tissue or organ rejection after transplantation. In particular embodiments the inflammatory disorder is selected from the group consisting of atherosclerosis, rheumatoid arthritis, osteoarthritis, sepsis and polyarthritis.

The invention also includes within its scope polypeptides having the amino acid sequence as set out in FIGS. 1*a-d* (SEQ ID NO: 2, 4, 6, and 8) or 2*a-d* (SEQ ID NO: 10, 12, 14 and 16), polynucleotides having the nucleic acid sequences as set out in FIGS. 1*a-d* (SEQ ID NO: 2, 4, 6, and 8) or 2*a-d* (SEQ ID NO: 10, 12, 14 and 16) and sequences having substantial identity thereto, for example, 70%, 80%, 85%, 90%, 95% or 99% identity thereto. The percent identity of two amino acid sequences or of two nucleic acid sequences is generally determined by aligning the sequences for optimal comparison purposes (e.g., gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proe. Natl. Acad. Sci. USA 87: 2264-2268, modified as in Karlin and Altschul (1993) Proc. Natl. Acad. Sci. USA 90: 5873-5877. The NBLAST and XBLAST programs of Altschul. et al. (1900) J. Mol. Biol. 215: 40.5-410 have incorporated such an algorithm. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25: 3389-3402. Alternatively, PSI-Blast can be used to perform an iterated search that detects distant relationships between molecules (Id.). When utilizing BLAST, Gapped BLAST, and PSI-Blast programs, the default parameters of the respective programs (e.g., XBLAST and NBLAST) can be used. Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm.

Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85: 2444-8. Within FASTA, ktup is a control option that sets the sensitivity and speed of the search.

The invention also include within its scope an antibody comprising a binding domain which binding domain comprises an amino acid sequence selected from the amino acid sequences represented by FIG. 1a to d (SEQ ID NO: 2, 4, 6, and 8) or 2a to d (SEQ ID NO: 10, 12, 14 and 16), or a variant thereof wherein said variant sequence has been altered by addition, substitution or deletion of at least one amino acid residue without substantially affecting the biological function of the antibody.

"Variant(s)" of polypeptides as used herein include polypeptides that differ in amino acid sequence from a reference polypeptide. Generally, differences are limited so that the sequences of the reference and the variant are closely similar and, in many regions, identical. A variant polypeptide may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine: b) glutamic acid and aspartic acid; c) asparagine and glutamine; d) arginine and lysine; e) isoleucine, leucine, methionine and valine; and f) phenylalanine, tyrosine and tryptophan.

One embodiment of the invention provides antibodies comprising a pair of binding domains based on the amino acid sequences for the VH and VL regions substantially as set out in FIGS. 1a-d (SEQ ID NO: 2, 4, 6 and 8) and 2a-d (SEQ ID NO: 10, 12, 14 and 16) respectively. Single binding domains based on either of these sequences form further aspects of the invention. In the case of the binding domains based on the amino acid sequence for the VH region substantially set out in FIGS. 1a-d (SEQ ID NO: 2, 4, 6 and 8), such binding domains may be used as targeting agents since it is known that immunoglobulin VH domains are capable of binding target antigens in a specific manner.

In the case of either of the single chain specific binding domains, these domains may be used to screen for complementary domains capable of forming a two-domain antibody which has in vivo properties as good as or equal to the monoclonal antibodies disclosed herein.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain antibody is selected in accordance with phage display techniques such as those described in that reference. This technique is also disclosed in Marks et al. ibid.

Antibodies of the present invention may further comprise antibody constant regions or parts thereof. For example, antibodies based on the VL region shown in FIG. 2 a-d (SEQ ID NO: 10, 12, 14 and 16) may be attached at their C-terminal end to antibody light chain constant domains including human CK or C# chains. Similarly, antibodies based on VH region shown in FIG. 1a-d (SEQ_ID NO: 2, 4, 6 and 8) may be attached at their C-terminal end to all or part of an immunoglobulin heavy chain derived from any antibody isotype, e.g. IgG, IgA, IgE and IgM and any of the isotype sub-classes.

Although antibodies of the invention have in themselves been shown to be effective in preventing cancer cell proliferation, they may additionally be labelled with a functional label. Functional labels include substances which are designed to be targeted to the site of cancer to cause destruction thereof. Such functional labels include toxins such as ricin and enzymes such as bacterial carboxypeptidase or nitroreductase, which are capable of converting prodrugs into active drugs. In addition, the antibodies may be attached or otherwise associated with chemotherapeutic or cytotoxic agents, such as calicheamicin, or radiolabels, such as 90Y or 11.

In an embodiment, the antibody of the invention is capable of inhibiting proliferation of a human adrenocarcinoma (SW-13) cell by at least 10%, wherein said inhibition is measured using a MTT Cell Proliferation assay. Preferably, the antibody is capable of modulating e.g. interfering with, interaction of RAMP-3 and CRLP.

Typically, the antibody is capable of inhibiting proliferation by at least 12%. In some embodiments, the antibody may be capable of inhibiting proliferation by at least 20% and optionally at least 25%. In a further embodiment, the antibody may be capable of inhibiting proliferation by at least 30% and further optionally at least 40%.

In one embodiment, the antibody is capable of reducing or inhibiting production of cAMP in a human MG63 osteosarcoma cell, when stimulated by adrenomedullin, by at least about 15%, e.g. at least 15%, 16%, 17%, 18% and 19%. In some embodiments, the antibody may be capable of inhibiting production of cAMP by at least about 20% e.g. 21%, 22% or 25%. Typically, the antibody is capable of modulating an interaction of RAMP-3 and CRLP.

The antibodies of the present invention may be generated wholly or partly by chemical synthesis. The antibodies can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing an antibody according to the present invention is to express the nucleic acid encoding it, by use of nucleic acid in an expression system.

The present invention further provides an isolated nucleic acid encoding an antibody of the present invention. Nucleic acid includes DNA and RNA. In a preferred aspect, the present invention provides a nucleic acid which codes for an antibody of the invention as defined above. Examples of such nucleic acid are shown in FIGS. 1a-d (SEQ ID NO: 1, 3, 5 and 7) and 2a-d (SEQ ID NO: 9, 11, 13 and 15). The skilled person will be able to determine substitutions, deletions and/or additions to such nucleic acids which will still provide an antibody of the present invention.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding an antibody of the invention forms an aspect of the present invention, as does a method of production of the antibody which method comprises expression from encoding nucleic acid therefore. Expression may conveniently be achieved by culturing under appropriate conditions recombinant host cells containing the nucleic acid. Following production by expression, an antibody may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art. For a review, see for example Pluckthun, BiolTechnology 9: 545-551 (1991). Expression in eukaryotic cells in culture is also available to those skilled in the art as an option for production of an antibody, see for recent review, for example Reff, Curr. Opinion Biotech. 4: 573-576 (1993); Trill et al., Curr. Opinion Biotech. 6: 553-560 (1995).

Suitable vectors can be chosen or constructed, containing appropriate regulatory sequences, including promoter sequences, terminator sequences, polyadenylation sequences, enhancer sequences, marker genes and other sequences as appropriate.

Vectors may be plasmids, viral e.g. 'phage, or phagemid, as appropriate. For further details see, for example, Sambrook et al., Molecular Cloning: A Laboratory Manual: 2nd Edition, Cold Spring Harbor Laboratory Press (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., Short Protocols in Molecular Biology, 2nd Edition, John Wiley & Sons (1992).

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express an antibody or polypeptide as above.

Methods of Diagnosis

Antibodies of the present invention can be used in methods of diagnosis of tumours in human or animal subjects.

Genes encoding RAMPs show elevated expression in specific cancer tissue. The expression of RAMP can be detected in a tissue or cell using the antibody of the present invention in a method such as Western blotting, the ELISA method or histological staining. A sample (such as biopsy sample or blood sample) derived from tissue of a subject is brought into contact with an antibody of the present invention under conditions so as to form an immune complex. The presence or the amount of the RAMP in the sample can be determined by determining whether the sample binds to the antibody. In this way, diagnosis of cancer, monitoring of progress or cure of cancer, and prediction of prognosis may be carried out.

In one embodiment the invention provides an in vitro method for detecting the presence of a tumour or inflammatory disorder in a biological sample, comprising the steps of contacting the biological sample with an antibody of the invention and detecting increased binding of the antibody relative to that detected in a negative control or in a biological sample from a normal healthy subject.

The invention also provides the use of an antibody of the invention in a method of diagnosis in vivo. In one embodiment the invention provides a method for detecting the presence of a tumour or inflammatory disorder in a subject, comprising the steps of administering to said subject the antibody of the invention and detecting increased binding of the antibody relative to that detected in a negative control or in a normal healthy subject.

The antibodies may be labelled or conjugated to other molecules to aid diagoistic imaging or other detection. For example, 123-iodine-radiolabeled antibody may be produced for detection by scintigraphy with single photon emission tomography with computerized tomography (SPECT/CT). Such methods may be combined with other diagnostic and imaging techniques where for example, 18F-fluorodeoxyglucose (18FDG) positron emission tomography with computerized tomography (PET/CT) may be performed. These techniques are known to those skilled in the art, and are exemplified in Birchler et al., Otolaryngology—Head and Neck Surgery, Volume 136, Issue 4, Pages 543-548).

In another embodiment the invention provides a method of monitoring the progression of a tumour or inflammatory disorder of a therapeutic regimen in a subject, comprising the steps of isolating a biological sample from the subject, contacting the biological sample with the antibody of the invention and detecting increased binding of the antibody relative to that detected in a negative control or in a biological sample from a normal healthy subject. In another embodiment the invention provides a method of monitoring the progression of a tumour or inflammatory disorder of a therapeutic regimen in a subject, comprising the steps of administering to said subject an antibody of the invention and detecting increased binding of the antibody relative to that detected in a negative control or in a normal healthy subject.

The biological sample to be tested may include any tissue from a subject such as biopsy tissue (e.g. tissue from tumours such as described herein or body fluid (e.g. blood).

When used in diagnosis, antibodies may be labelled with a detectable label, for example a radiolabel such as I or 99Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Products, Pharmaceutical Compositions and Therapeutic Uses

The antibodies of the present invention may be administered alone or in combination with other treatments, either simultaneously or sequentially, dependent upon the condition to be treated. Thus, the present invention further provides products containing an antibody of the present invention and an active agent as a combined preparation for simultaneous, separate or sequential use in the treatment of a tumour. Active agents may include chemotherapeutic or cytotoxic agents including, 5-Fluorouracil, cisplatin, Mitomycin C, oxaliplatin and tamoxifen, which may operate synergistically with the antibodies of the present invention. Other active agents may include suitable doses of pain relief drugs such as non-steroidal anti-inflammatory drugs (e.g. aspirin, paracetamol, ibuprofen or ketoprofen) or opiates such as morphine, or anti-emetics.

Whilst not wishing to be bound by theory, the ability of the antibodies of the invention to synergise with an active agent to enhance tumour killing may not be due to immune effector mechanisms but rather may be a direct consequence of the antibody binding to cell surface RAMP.

Antibodies of the present invention will usually be administered in the form of a pharmaceutical composition, which may comprise at least one component in addition to the antibody. The pharmaceutical composition may comprise, in addition to active ingredient, a pharmaceutically acceptable excipient, diluent, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

It is envisaged that systemic injections by normal routes (such as intravenous, intra-arterial, peritoneal, intramuscular or subcutaneous injection) will be the primary route for therapeutic administration of the compositions although local delivery by local injection or through a catheter or other surgical tubing may also used as may local injection or infusion by an indwelling reservoir minipump or other slow-release device. Local administration may be into the pathological tissue mass or into a body cavity that contains the target tissue. Examples of such cavities may include the cerebral ventricles, the synovial joints or the pleural cavity. Liquid formulations may be utilised after reconstitution from powder formulations.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil.

Physiological saline solution, dextrose or other saccharide solution or glycols such as ethylene glycol, propylene glycol or polyethylene glycol may be included. Where the formulation is a liquid it may be, for example, a physiologic salt solution containing non-phosphate buffer at pH 6.8-7.6, or a lyophilised powder.

The composition may also be administered via microspheres, liposomes, other microparticulate delivery systems or sustained release formulations placed in certain tissues including blood. Suitable examples of sustained release carriers include semi-permeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22 (1): 1985), poly(2-hydroxyethyl-methacrylate) or ethylene vinyl acetate (Langer et al, J. Biomed. Mater. Res. 15: 167-277, 1981, and Langer, Chem. Tech. 12:98-105, 1982).

Liposomes containing the polypeptides are prepared by well-known methods: DE3,218, 121A; Epstein et al, PNAS USA, 82: 3688-3692, 1985; Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. Nos. 4,485,045 and 4,544,545.

Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

The composition may be administered in a localised manner to a tumour site or other desired site or may be delivered in a manner in which it targets tumour or other cells.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of existing tumours, especially cancer, and in the prevention of the recurrence of such conditions after initial treatment or surgery. Examples of the techniques and protocols mentioned above can be found in Remington's Pharmaceutical Sciences, 16th edition, Oslo, A. (ed), 1980.

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m of antibody provides a serum concentration of approximately 20 nM for approximately eight days.

The dose of the composition will be dependent upon the properties of the antibody, e.g. its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. This invention is also directed to optimise immunisation schedules for enhancing a protective immune response against cancer.

An antibody or composition according to the invention may be useful in the treatment, retardation and/or prevention of a proliferative disorder such as a tumour through, for example, the inhibition of angiogenesis or cancer cell proliferation.

Specific examples of the tumours to be treated according to the invention include lung, intracranial (including brain) and skin tumours. Preferred are intracranial tumours for example brain tumours. Lung tumours or cancer may be classified into small cell carcinoma, adenocarcinoma, large cell carcinoma, bronchioalveolar, squamous and carcinoid. Any lung tumour may be treated according to the invention. Skin tumours or cancer may be classified into melanoma, oral squamous and teratocarcinoma. Intracranial and brain tumours may be classified into glioma, glioblastoma, neuroblastoma, pituitary adenoma, somatotropinomas, prolactinomas, meningiomas, astrocytomas and Choroid plexus carcinoma. Adrenal tumours may be classified into adrenocortical carcinoma, pheochromocytoma, aldosteronoma. The tumour may be an ocular tumour.

The tumour to be treated may be selected from the group consisting of osteosarcoma, adrenocarcinoma, glioblastoma, prostate tumour, breast tumour and mesothelioma. The tumour to be treated may be a brain tumour for example a glioblastoma.

The tumour to be treated may be an adrenal tumour for example an adrenocortical carcinoma.

The tumour to be treated may be mesothelioma.

The tumour to be treated may be a bone tumour for example an osteosarcoma.

The tumour to be treated may be a prostate tumour.

The tumour to be treated may be a tumour of the breast.

The tumour to be treated may be a colon tumour.

In one embodiment, the antibody of the invention useful in the treatment of a tumour is a RAMP (e.g. RAMP 3) antagonist.

Other proliferative disorders to be treated may include hyperkeratosis.

An antibody or composition according to the invention may be useful in the treatment, retardation and/or prevention of an inflammatory disorder such as defined herein. In one embodiment, the antibody of the invention useful in the treatment of an inflammatory disorder is a RAMP (e.g. RAMP 3) antagonist.

An antibody or composition according to the invention may be useful in the treatment, retardation and/or prevention of a cardiovascular condition through, for example, the promotion of angiogenesis and vasulogenesis. Specific examples of a cardiovascular condition may include heart failure, stroke (specifically re-vasculariation after stroke), coronary heart disease, vascular disease, myocardial infarction (specifically re-vasculariation after myocardial infarction) and diabetic angiopathy and specifically retinopathy. In one embodiment, the antibody of the invention useful in the treatment of a cardiovascular condition is a RAMP (e.g. RAMP 3) agonist.

An antibody or composition according to the invention may also be useful in the treatment of a disorder selected from pre-eclampsia. pancreatitis (e.g. acute pancreatitis), osteoporosis, obesity, toxicity (e.g. lead toxicity), sepsis and wounds. As used herein the term "wound" includes ulcers and lesions, for example cutaneous wounds such as cuts or burns, and conditions associated therewith. The antibody or composition of the invention may be used to stimulate proliferation and tissue growth such as wound healing generally. This might include healing of skin wounds after surgery where an accelerator of healing could have benefits, healing of open skin wounds where there is skin or tissue loss, healing of ulcers whether due to diabetes, pressure sores in bed rest patients or other causes, healing of delayed tissue repair such as in delayed or non-union of bone fractures, repair of cartilage and joint tissues after injury with or without surgery, healing of tendon injuries such as Achilles tendon ruptures and tendon injuries in horses. Other indications would include treatment of tissue loss such as occurs in osteoporosis. In one embodiment, the antibody of the invention useful in the treatment of hypertension, obesity, wounds and osteoporosis is a RAMP (e.g. RAMP 3) agonist. Alternatively the antibody useful in the treatment of osteoporosis may be a RAMP (e.g. RAMP 3) antagonist.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

FIG. 1a-d shows the nucleic acid (SEQ ID NO: 1, 3, 5 and 7) and amino acid (SEQ ID NO: 2, 4, 6 and 8) sequences of the heavy chain variable region of monoclonal anti-RAMP 3 antibodies;

FIG. 2 a-d shows the nucleic acid (SEQ ID NO: 9, 11, 13 and 15) and amino acid (SEQ ID NO: 10, 12, 14 and 16) sequences of the light chain variable region of monoclonal anti-RAMP 3 antibodies;

FIGS. 3 to 6 show the amino acid sequences of the heavy chain of a monoclonal anti-RAMP 3 antibody (SEQ ID NO: 17-36);

FIGS. 7 to 10 show the amino acid sequences of the light chain of a monoclonal anti-RAMP 3 antibody (SEQ ID NO: 37-56);

DETAILED DESCRIPTION

Examples

Figure 11:
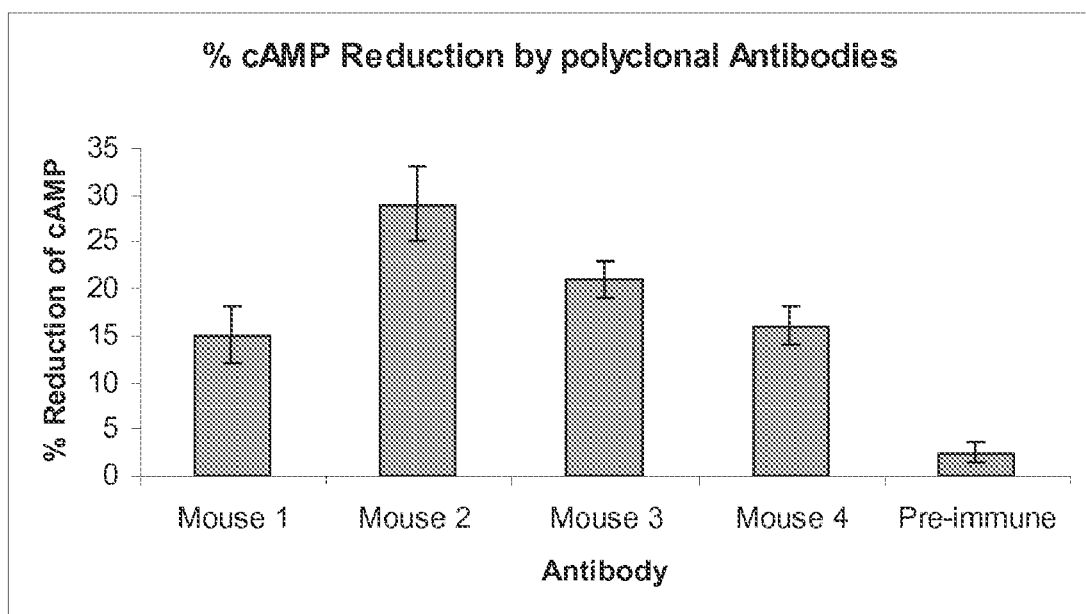
FIG. 11 Polyclonal anti-RAMP-3 antibodies were tested for their ability to regulate the effect of adrenomedullin to increase cyclic AMP in human MG63 osteosarcoma cells. All antibodies reduced the effect of adrenomedullin.

The invention will now be described further in the following non-limiting example:

Materials and Methods

Generation of the RAMP Extra Cellular Domain (ECD) Protein

The ECD regions of the RAMP were generated using a high fidelity PCR reaction using KOD Hot Start DNA Polymerase kit from Novagen Toyobo. The template DNA was obtained from a purchased sample of human brain cDNA (Ambion).

This reaction was carried out twice the first reaction was carried out to isolate a region larger than the whole RAMP ECD using the following primers:

```
RAMP1
Forward
CGAGCGGACTCGACTCGGCAC (SEQ ID NO: 57)

Reverse
CTTCCTAGGGTGGCGGTGGCC (SEQ ID NO: 58)

RAMP2
Forward
GTC CGC CTC CTC CTT CT GCT
(SEQ ID NO: 59)

Reverse
AAG TGG AGT AAC ATG GTT ATT GT
(SEQ ID NO: 60)

RAMP3
Forward
AGC CAT GGA GAC TGG AGC GCT GC
(SEQ ID NO: 61)

Reverse
GTG GCC CAG TAG CTG GAG ATT GGC
(SEQ ID NO: 62)
```

The second PCR reaction uses the products from the reaction using the primers above. Using the primers below these primers have had EcoR1 and BamH1 restriction sites incorporated into them:

```
RAMP1
Forward
GCGAATTCCTGCCAGACCACCAG (SEQ ID NO: 63)

Reverse
GTGGATCCTACCGGGCCCGGGACA (SEQ ID NO: 64)

RAMP2
Forward
GCG AAT TCA ATC CCC ACG AGG CCC TGG CTC AGC C
(SEQ ID NO: 65)

Reverse
CAG GAT CCTACA AGA GTG ATG AGG AAG GGG ATG
(SEQ ID NO: 66)

RAMP3
Forward
CAG AATT TCC AGA GCA GGC CGC TGC AAC CAG ACA G
(SEQ ID NO: 67)
```

-continued

```
Reverse
GTG GAT CC C ACC ACC AGG CCA GCC ATG GCG ACA GT
(SEQ ID NO: 68)
```

Genomic sequencing of the product is performed to test the product conclusively. The ECD protein from this point onwards will be referred to as "the insert" unless stated otherwise.

Protein Purification

The ECD peptides were expressed and purified. The protein was purified using the Glutathione S-transferase (GST) gene fusion system.

Antibody Generation.

Antibodies to the ECD peptides were generated using the following protocol.

Mouse and Rat Immunisation Protocol.

The following immunization protocol was followed to raise antibodies against the extracellular domain of RAMP-3:

Pre-immune serum was taken from the mice prior to immunisation. Four mice were injected with a peptide corresponding to an extracellular domain of RAMP-3:

```
        10        20 30        40   50        60
    GCPRAGGCNE TGMLERLPLC GKAFADMMGK VDVWKWCNLS
    (SEQ ID NO: 69)

70        80         90  99
    EFIVYYESFT NCTEMEANVV GCYWPNPLAQ GFITGIHRQF

FSNCTVDRVH LEDPPDEVL (SEQ ID NO: 70)
```

Injections were boosted with 4 further injections, at approximately monthly intervals. Sample bleeds from the mice were taken to isolate serum containing polyclonal antibodies. The adjuvant used was Freunds (complete for the first injection, followed by incomplete for the rest of the course). The total volume that can be injected into rodents is 0.2 ml (and preferably no more than 0.1 ml for mice). Half of this will be antigen and half adjuvant therefore the antigen should be of sufficient concentration to provide the required number of milligrams in a maximum of 0.1 ml or 0.05 ml injected.

Western Blots Protocol

Western blots of the antibodies were used to probe blots of the original ECD peptide run in duplicate lanes with a size marker. Antibody 1 and 2 show clear binding to the protein bands at the expected size of 14 KDa (data not shown). Antibody 3 shows very strong binding at the same size, while AB4 was not detectable in this experiment (data not shown).

Antibody Blocking Potential.

To test the ability of the antibodies to bind to RAMP, assays were carried out to determine the antibodies' blocking potential:

Human MG63 osteosarcoma cells were treated with 10 pmol of AM and the cAMP response measured (method as stated above e.g. using cAMP Fluorescence Polarization (FP) Biotrak™ Immunoassay (Amersham Biosciences)). (If RAMP-1 agents are being tested, this assay can also be carried out using CGRP as a ligand to test the agent's blocking ability).

The cells were pre-treated with the antibody for 1 hr
An $EC_{50}$ dose of AM was applied (10 pmol) was applied and cAMP response was measured.

The polyclonals were used to test their ability to regulate the effect of adrenomedullin to increase cyclic AMP in human MG63 osteosarcoma cells.

Monoclonal Antibody Production

Monoclonal antibodies were produced using the $3^{rd}$ mouse. The methods used to produce the monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

Clones were screened and selected on the basis of not binding to the GST tag on the peptide. Of these clones, ELISA data was obtained and the best 5 were selected for further work.

Antibody Isotyping

Characterisation of the monoclonal antibody's isotype was determined using the isotyping kit, IsoStrip™ (Roche Diagnostics GmbH).

The isotypes of the monoclonal antibodies are as follows:
CD12-IgG-IgG1 subtype
HB10-IgG-IgG1 subtype
JF2-IgG-IgG1 subtype
JB3-IgM
CC2-IgA Proliferation Assays Cell Culture The cell culture was carried out under aseptic conditions on Nunclon™ treated tissue culture plastics. The U-87 glioblastoma cells (ATCC noHTB-14) used for this project were cultured in standard EMEM (Earle's Minimum Essential Medium) media (Gibco) with 10% Fetal Calf Serum (Gibco) and 5% Penicillin/Streptomycin antibiotic (Sigma). The frozen cells were thawed at 37° C. for 2 minutes. The cells were then immediately transferred to 75 cm2 flask with 10 ml of media. The culture was incubated at 37° C. with 5% CO2 to attain confluency. The media was changed every three days and the cells were then subcultured after reaching 80-90% confluency. Cells were washed with PBS (Gibco) to remove serum present because it acts as an inhibitor for trypsin. 3 ml of 10% Trypsin EDTA (Sigma) was added to remove the cell layer from the flask. The trypsinization was allowed to occur for 15 minutes at 37° C. in order to facilitate dispersal. The flask was observed under a microscope to confirm that the cells have detached from the flask. 6-8 ml of media was added to the flask and the cells were aspirated gently. The cells were centrifuged at 1000 rpm for 3 minutes and the supernatant was discarded, the resulting cell pellet was resuspended in 1 ml of media and subcultured into the appropriate number of flasks at a ratio of 1:6.

Preparation of Plates

The U87 glioblastoma cells were grown under standard conditions (as mentioned above). The total number of cells were counted using a haemocytometer (Hawksley) and the concentration was calculated using the following equation:

$$\text{Total cell count per ml} = \frac{\text{average cell count (5 squares)}}{0.02}$$

The cell concentration was adjusted to 2000 cells per 50 µl. 50 µl of the above cell preparation were seeded in clear 96 well plates (Costar, polystyrene, Flatbottom).

Experimental Conditions

Two groups of proliferation studies were carried out for each antibody. One group was used to study the effect on proliferation by the antibody in presence of endogenous adrenomedullin, while the other group was used to the study the effects of antibody in presence of exogenously added adrenomedullin. Varying concentrations of antibody were prepared in PBS to result in final well concentrations of 10 μg, 1 μg, 100 ng, 10 ng, 1 ng, 100 pg, 10 pg and 1 pg. Six replicates of each concentration of each antibody was carried out. This dose range was used in both groups. Adrenomedullin was added to the appropriate group to a final well concentration of 200 nM. 5-FluoroUracil (Fluka) was used as a positive control (100 mM) for the reduction in proliferation. PBS controls were also prepared. The plates were then incubated under standard conditions. Replacement and re-dosing of antibody and controls was carried out every 2 days. Mouse anti-GST antibody concentration responses were also calculated the similar way since it was the antibody control for the experiment Assay Procedure In order to check for consistency of the cells seeded, a 12-24 hours study was performed. Further time points were carried out at 2, 4, 6 and 8 days. The kit used to perform the proliferation assay was MTT Cell Proliferation Assay (ATCC). At each time point 10 μl of MTT reagent was added to all the wells and left to incubate at 37° C. for 2 hours. After 2 hours, 100 μl of MTT detergent was added to the wells and incubated overnight and agitated in the dark. The plate was read for absorbance at 595 nM (Spectramax M5e), using the software Softmax™ Pro 5.2.X 100035.

The proliferation/survival of SW-13 and U87 (Glioblastoma cell line) cells was determined using the MTT assay.

Apoptosis Assay

The apoptosis assay was carried out using the Caspase-3 Assay kit (Sigma).

Cell Preparation

U-87 cells were prepared under standard conditions. A cell solution of $2 \times 10^7$ cells was made up in 2 ml of media were dispensed into polypropylene tubes.

Experimental Conditions $2 \times 10^7$ cells wens taken for each treatment. The treatment groups were, antibody treated cells (for each antibody), anti-Fas antibody, antibody and adrenomedullin treated cells, blank and adrenomedullin treated cells. The positive control used was anti-Fas monoclonal antibody (MBL). The final concentration of antibodies used was 10 g and for anti-Fas antibody was 500 ng. The anti-Fas antibody is an IgM antibody and possesses cytolytic activity thereby inducing apoptosis to the cells.

The treated cell suspension in 2 ml media were incubated for 3 hours at 37° C. in a 5% CO2 atmosphere.

Assay Procedure

The assay buffer and lysis buffer given in the kit was prepared using the given 17 megohm water as per the standard instructions given in the protocol. After 3 hours of incubation, the cells were centrifuged at 600 g for 5 minutes at 4° C. The supernatant was discarded and the cells were resuspended in 1 ml PBS. The cells were once again centrifuged using the above mentioned conditions and the supernatant was discarded. The cell pellet was resuspended in 200 μl 1× lysis buffer and incubated on ice for 20 minutes. The lysed cells were centrifuged at 20,000 g for 15 minutes at 4° C. The cell lysine were then laid out in a 96 well flat bottomed plate as shown in FIG. 6 and incubated overnight. The absorbance was read at 405 nm (Spectramax M5e), using the software Softmax™ Pro 5.2.36.

Animal Studies

Cell Culture of Cells for Xenografting

MDA-MB-436-GFP cells were cultured in RPMI media containing penicillin (50 U/ml), streptomycin (50 μg/ml), glutamine (1 mg/ml), and supplemented with 10% fetal bovine serum. Cells were cultured under a humid 5% $CO_2$/95% air atmosphere, and fed with fresh medium every 2 days, being routinely monitored for mycoplasma contamination. Cells growing exponentially were harvested using Trypsin EDAT solution. All culture media components were purchased from Invitrogen Life Technologies Animal Conditions Animal work was performed in the animal facility of the University of Sheffield. Male 4-to-5-week-old CD1 nude (nu/nu) mice were used. Mice were acclimated and housed in sterile cages in groups of four or less under laminar flow hoods in a temperature-controlled room with a 12-hour light/12-hour dark schedule, and fed autoclaved chow and water ad libitum.

Treatment and Xenograft

CD1 nude (nu/nu) nude mice were implanted with MDA-MB-436-GFP breast cancer cells. For the cell implantations, MDA-MB-436-GFP cells, grown in culture, were washed with PBS, dispersed in a 0.05% solution of trypsin, and resuspended. After centrifugation (1000 rpm for 3 minutes at 8° C.), the cell pellet was resuspended in PBS and the final concentration was adjusted to $3 \times 10^7$ cells/ml and the suspension was placed on ice. After the site was cleaned with ethanol, 0.1 ml ($0.5 \times 10^6$ cells) of the suspension were subcutaneously injected in the right flanks of nude mice. Tumors were measured with a digital venier calliper (Site), and tumour volumes were determined using the formula width×length×height×0.52 (for ellipsoid form), these measurement were taken twice weekly. Tumours were allowed to develop for 21 days, animals were randomly divided into three groups. One group (n=8) received interperotanial injection of JB3 antibody (200 μg of purified IgG) as a suspension in PBS in a volume of 0.2 ml every Tuesday and Friday of each week. As control, one group (n=8) received an irrelevant antibody (IgG of the same isotype, an inactivated form of the antibody) and the other group (n=8) received comparable injections of the vehicle alone (PBS). Schedule 1 was performed at the indicated time.

Tumour Sectioning

Tumours were excised from mice following euthanasia and fixed in 10% formalin saline solution. Tumour sections were embedded in parafin (standard protocol). Sections were cut at 5 μm, through the tumour body. Sections of each specimen were stained using haematoxylin and eosin (H&E) and mounted with glass cover slips.

Results

All polyclonal antibodies tested reduced the effect of adrenomedullin on cAMP production. The results shown in FIG. 11 indicate that the polyclonal antibodies raised against RAMP-3 inhibited cAMP production of the MG63 cells by at least 15%.

Figure 12:
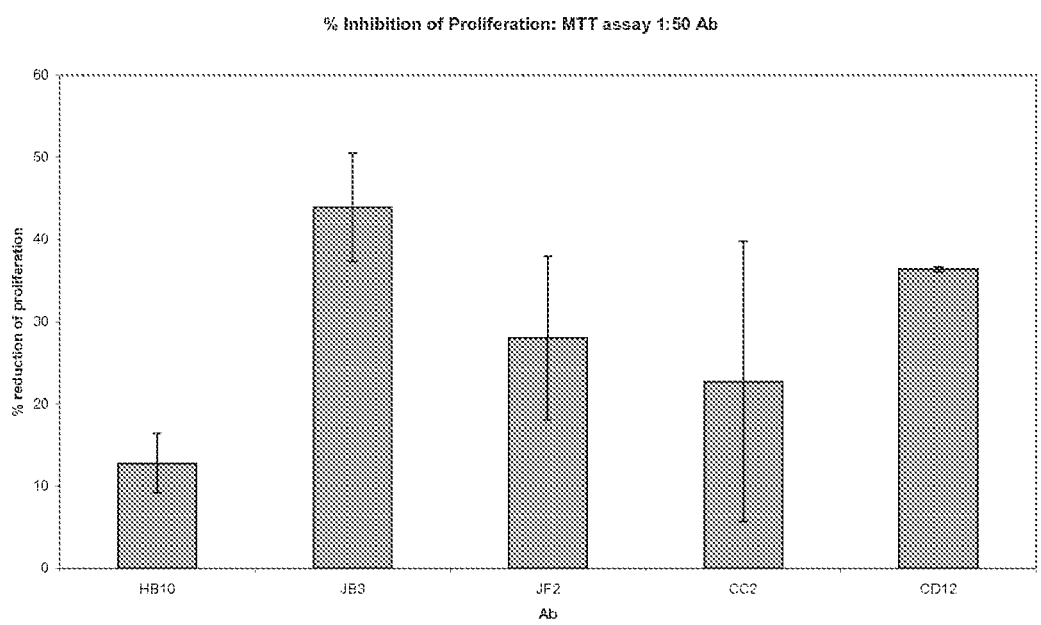
FIG. 12: shows the effect of the monoclonal antibodies on the growth of SW-13 cells in vitro. Monoclonal anti-RAMP-3 antibodies were tested for their ability to induce inhibition of proliferation of SW-13 (adenocarcinoma cells). The concentration of 1:50 equates to about 5 ng per well final concentration.

Each monoclonal antibody produced induced inhibition of proliferation of SW-13 cells ranging from 12-45% see FIG. 12 (the concentration of 1:50 equates to about 5 nano-grammes per well final concentration).

Figure 13:
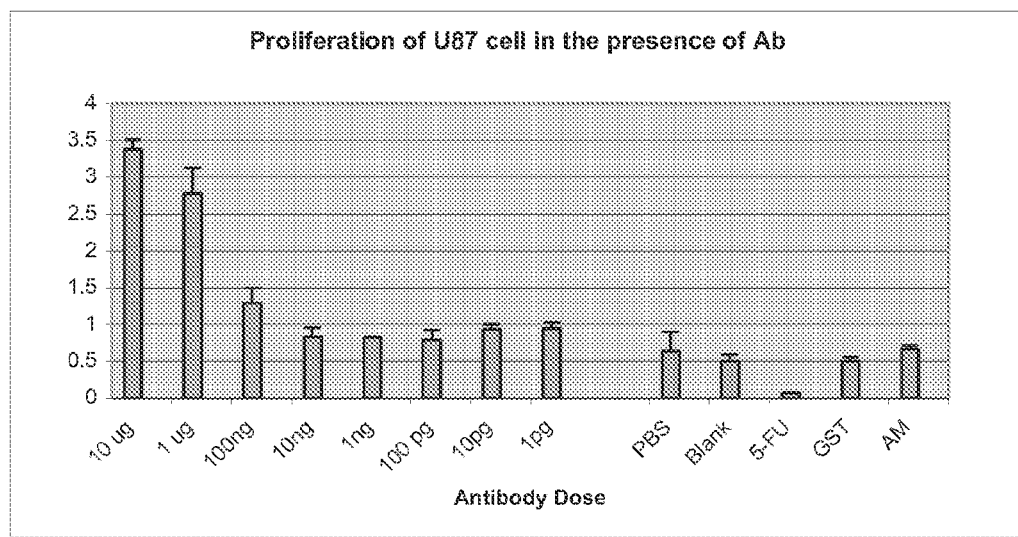
FIG. 13: shows the effect of monoclonal antibody HB10 on the growth of U87 cells in vitro. Tumour cells were seeded at 2000 cells in 96 well plates, AM at 2×10-7 and a dose range of antibody were added. As controls a non mammalian IgG antibody was added. This treatment regime was carried out every 2 days. At day 4 the cells were prepared for MTT assay ATTC.

One of the monoclonal antibodies tested, HB10, increased proliferation of U87 cells (see FIG. 13). As the dose of antibody increased so did the level of absorbance and therefore for the level of proliferation suggesting an agonist role for this antibody.

Figure 14:
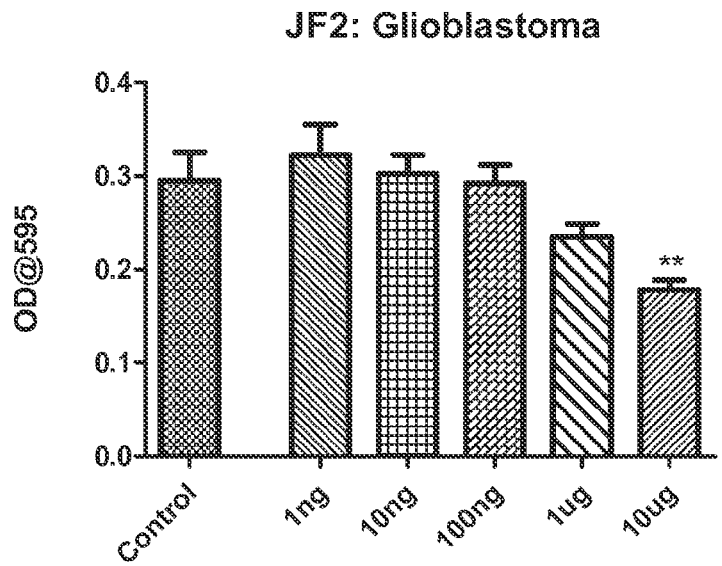
FIG. 14 shows a MTT assay assessing the rate of proliferation in the U-87 glioblastoma cell line in the presence of antibody JF2 at varying concentrations (after 8 days of culture).

FIG. 14 shows a MTT assay assessing the rate of proliferation in the U-87 glioblastoma cell line in the presence of antibody JF2 at varying concentrations (after 8 days of culture). Compared to controls a 10 μg dose of antibody JF2 produced a significant reduction in proliferation, this represents a 40% reduction in proliferation.

Figure 15:
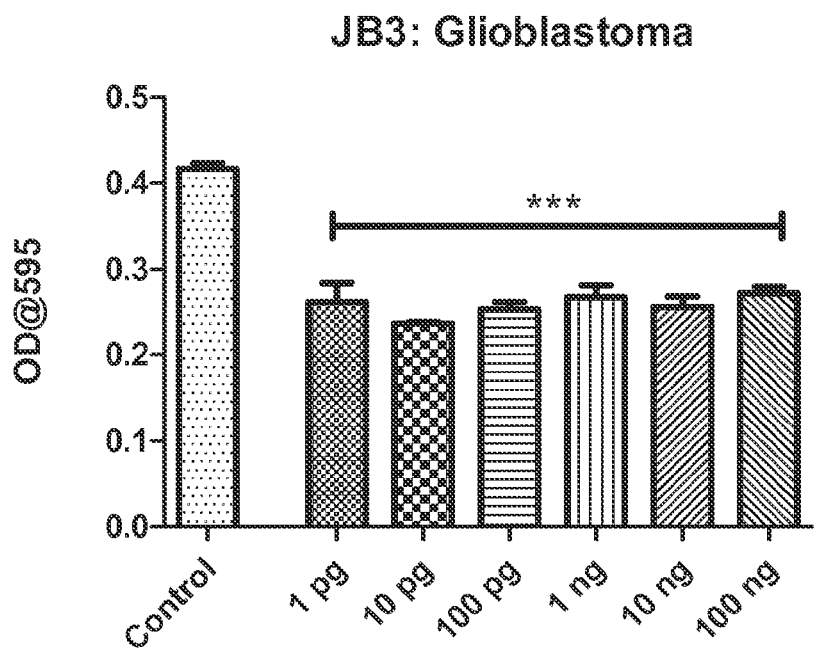
FIG. 15 shows a MTT assay assessing the rate of proliferation in the U-87 glioblastoma cell line in the presence of antibody JB3 at varying concentrations (after 8 days of culture).

FIG. 15 shows a MTT assay assessing the rate of proliferation in the U-87 glioblastoma cell line in the presence of antibody JB3 at varying concentrations (after 8 days of culture). Compared to controls all dose of antibody JB3 produced a significant reduction in proliferation, this represents a ~35% reduction in proliferation at all doses. This suggests an EC50 to be lower than 1 pg.

Figure 16:
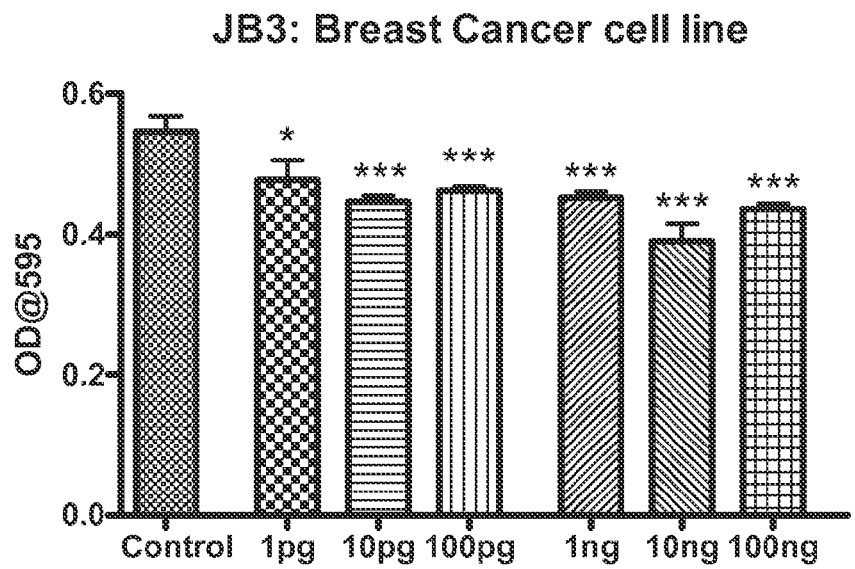
FIG. 16 shows a MTT assay assessing the rate of proliferation in the MDA-MB-436-GFP breast cancer cell line in the presence of antibody JB3 at varying concentrations (after 8 days of culture).
Figure 17:
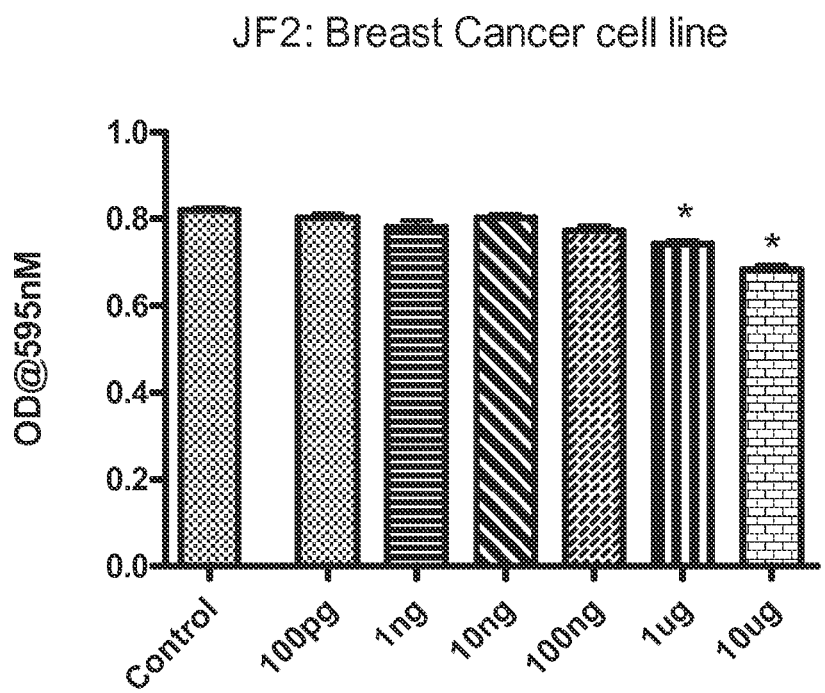
FIG. 17 shows a MTT assay assessing the rate of proliferation in the MDA-MB-436-GFP breast cancer cell line in the presence of antibody JF2 at varying concentrations (after 8 days of culture).

FIG. 16 shows a MTT assay assessing the rate of proliferation in the MDA-MB-436-GFP breast cancer cell line in the presence of antibody JB3 at varying concentrations (after 8 days of culture). Compared to controls all dose of antibody JB3 produced a significant reduction in proliferation however no dose response was observed. 10 ng produced the greatest reduction of 29% however this response does not significantly differ from the other treated groups FIG. 17 shows a MTT assay assessing the rate of proliferation in the MDA-MB-436-GFP breast cancer cell line in the presence of antibody JF2 at varying concentrations (after 8 days of culture). Compared to controls doses 1 μg and 10 μg of antibody JF2 produced a significant reduction in proliferation. 10 μg produced the greatest reduction of 12%.

Figure 18:
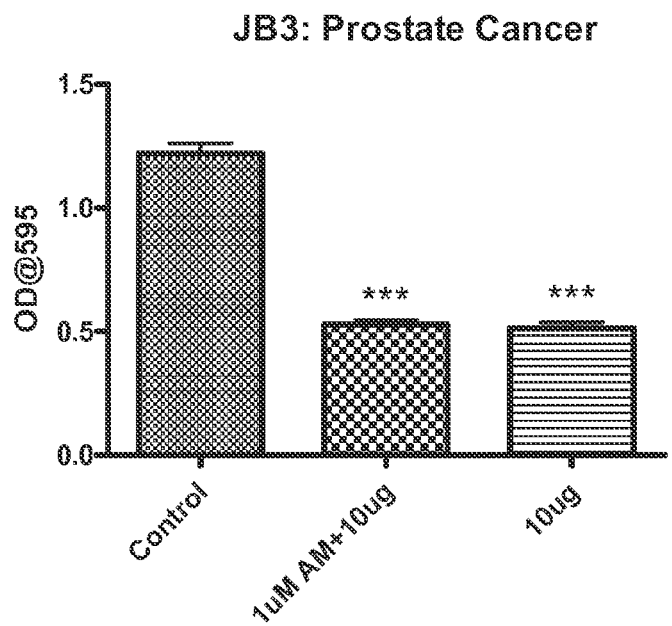
FIG. 18 shows a MTT assay assessing the rate of proliferation in the PC-3 prostate cancer cell line in the presence of antibody JB3 at a concentration of 10 μg (after 8 days of culture).

FIG. 18 shows a MTT assay assessing the rate of proliferation in the PC-3 prostate cancer cell line in the presence of antibody JB3 at a concentration of 10 μg (after 8 days of culture). Compared to controls doses 10 μg of antibody JB3 produced a significant reduction in proliferation both in the presence and absence of exogenously added adrenomedullin. 10 μg produced a 57% reduction in proliferation.

Figure 19:
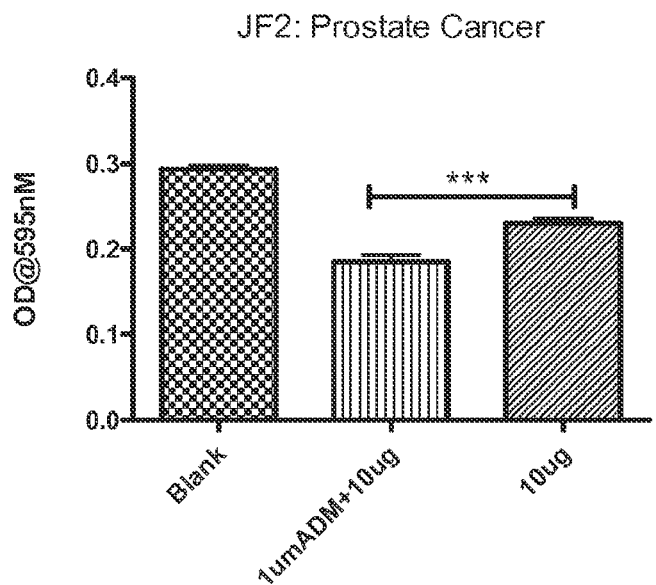
FIG. 19 shows a MTT assay assessing the rate of proliferation in the PC-3 prostate cancer cell line in the presence of antibody JF2 at a concentration of 10 μg (after 8 days of culture).

FIG. 19 shows a MTT assay assessing the rate of proliferation in the PC-3 prostate cancer cell line in the presence of antibody JF2 at a concentration of 10 μg (after 8 days of culture). Compared to controls doses 10 μg of antibody JF3 produced a significant reduction in proliferation both in the presence and absence of exogenously added adrenomedullin. 10 μg of JF2 in the presence of adrenomedullin produced a 37% reduction in proliferation and 22% reduction in the absence of exogenously added adrenomedullin.

Figure 20:
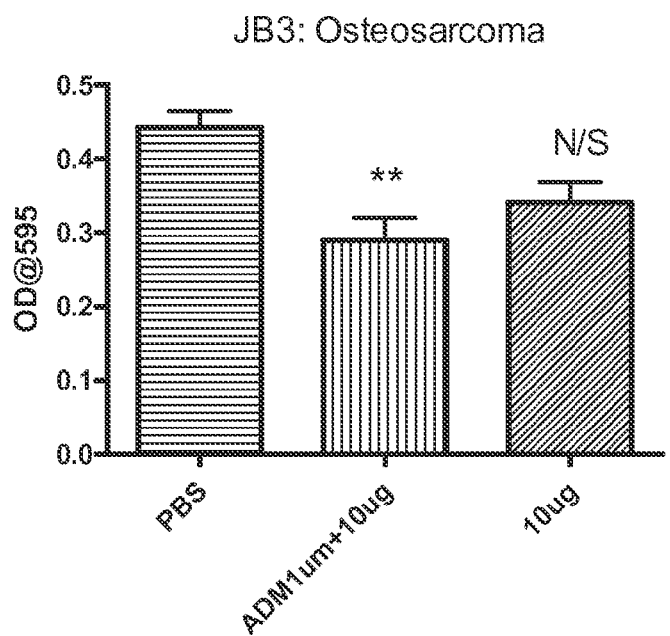
FIG. 20 shows a MTT assay assessing the rate of proliferation in the SAOS osteosarcoma cell line in the presence of antibody JB3 at a concentration of 10 μg (after 8 days of culture).

FIG. 20 shows a MTT assay assessing the rate of proliferation in the SAOS osteosarcoma cell line in the presence of antibody JB3 at a concentration of 10 μg (after 8 days of culture). Compared to controls doses 10 μg of antibody JB3 produced a significant reduction in proliferation both in the presence, however no significant reduction was observed in the absence of exogenously added adrenomedullin. 10 μg of JB3 in the presence of adrenomedullin produced a 34% reduction in proliferation.

Figure 21:
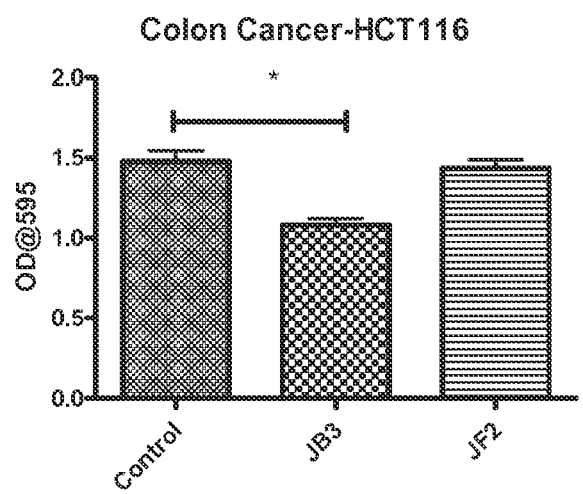
FIG. 21 shows a MTT assay assessing the rate of proliferation in the HCT116 colon cancer cell line in the presence of antibody JB3 and JF2 at a concentration of 10 μg (after 8 days of culture).

FIG. 21 shows a MTT assay assessing the rate of proliferation in the HCT116 colon cancer cell line in the presence of antibody JB3 and JF2 at a concentration of 10 μg (after 8 days of culture). Compared to controls doses 10 μg of antibody JB3 produced a significant reduction in proliferation; however JF2 produced no statistically significant reduction in proliferation. 10 μg of JB3 in the presence of adrenomedullin produced a 27% reduction in proliferation.

Figure 22:
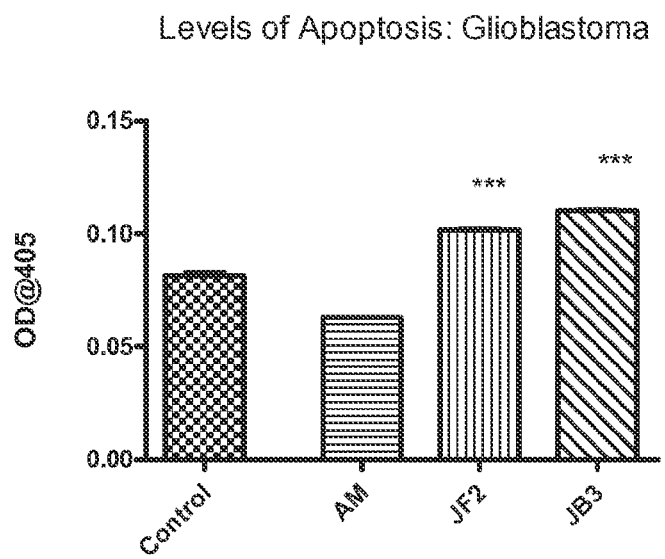
FIG. 22 shows an apoptosis assay assessing the levels of caspase-3 a marker in U-87 glioblastoma cancer cell line in the presence of antibody JB3 and JF2.

FIG. 22 represents levels of apoptosis, by measure levels of caspase-3 a marker apoptosis. U-87 glioblastoma cancer cell line in the presence of antibody JB3 and JF2 at a concentration of 10 μg both showed a significant increased in the levels of caspase-3 and their for apoptosis. Treated groups represent a 26% increase levels of caspase-3

Figure 23:
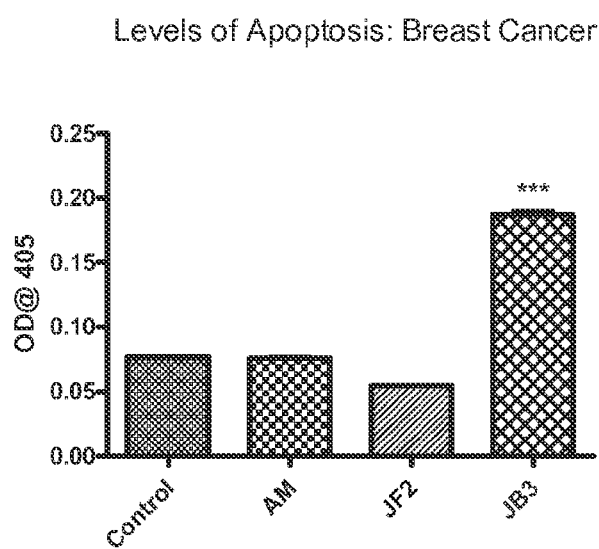
FIG. 23 shows an apoptosis assay assessing the levels of caspase-3 a marker in a MDA-MB-436-GFP breast cancer cell line in the presence of antibody JB3 and JF2.

FIG. 23 represents levels of apoptosis, by measure levels of caspase-3 a marker apoptosis. MDA-MB-436-GFP breast cancer cell line in the presence of antibody JB3 and JF2 at a concentration of 10 μg only antibody JB3 showed a significant increased in the levels of caspase-3 and their for apoptosis. The JB3 treated group represents a 59% increase in caspase-3.

Figure 24:
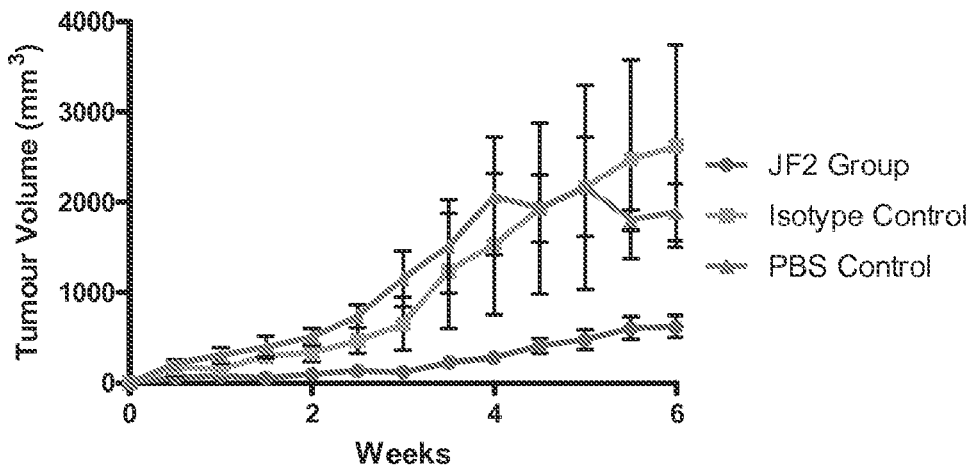
FIG. 24 represents the tumour volume of MDA-MB-436-GFP injected into the right flank of CD1 nude mice, treated with JF2 antibody and controls over a period of 6 weeks.

FIG. 24 represents the tumour volume of MDA-MB-436-GFP injected into the right flank of CD1 nude mice, treated with JF2 antibody and controls over a period of 6 weeks. Both control groups show large tumour volumes increases after week 3, however rates of growth within the treatment groups are considerably slower. Error bars within the control groups are large throughout the experiment however within the treatment groups errors are consistently small.

Figure 25:
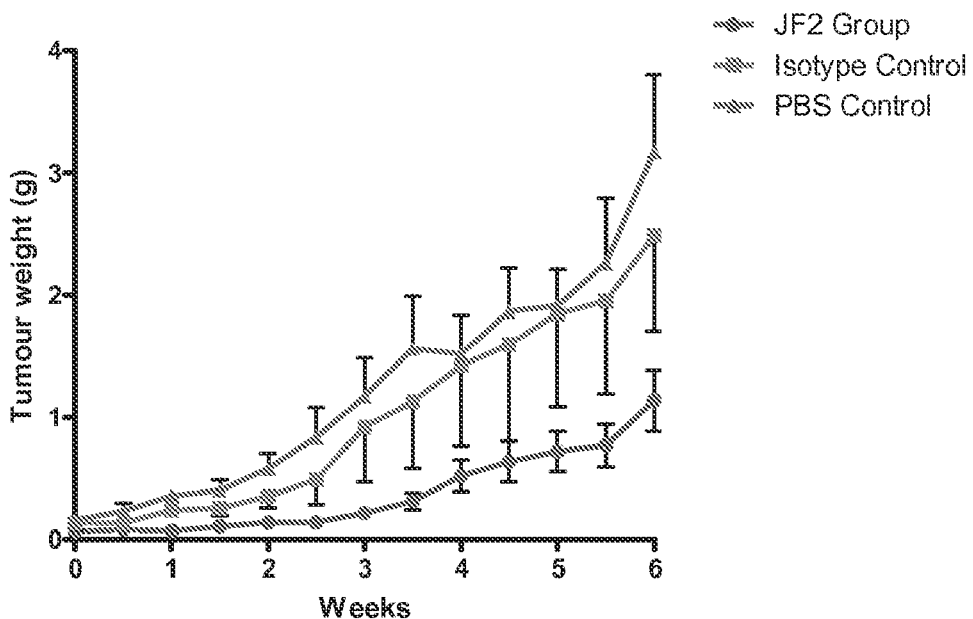
FIG. 25 represents the tumour weights of MDA-MB-436-GFP injected into the right flank of CD1 nude mice, treated with JF2 antibody and controls over a period of 6 weeks.

FIG. 25 represents the tumour weights of MDA-MB-436-GFP injected into the right flank of CD1 nude mice, treated with JF2 antibody and controls over a period of 6 weeks. Tumour weights are taken following death and calculated back using the volumes of tumours. Control groups show increases in weight from early time points, however treated groups show slower growth until weeks 4 were weighs increase however still remain below control groups.

Figure 26:
FIG. 26 show fluorescence of the MDA-MB-436-GFP cancer cell lines injected into the right flank of nude mice.

FIG. 26 show fluorescence of the MDA-MB-436-GFP cancer cell lines injected into the right flank of nude mice.

Figure 27:
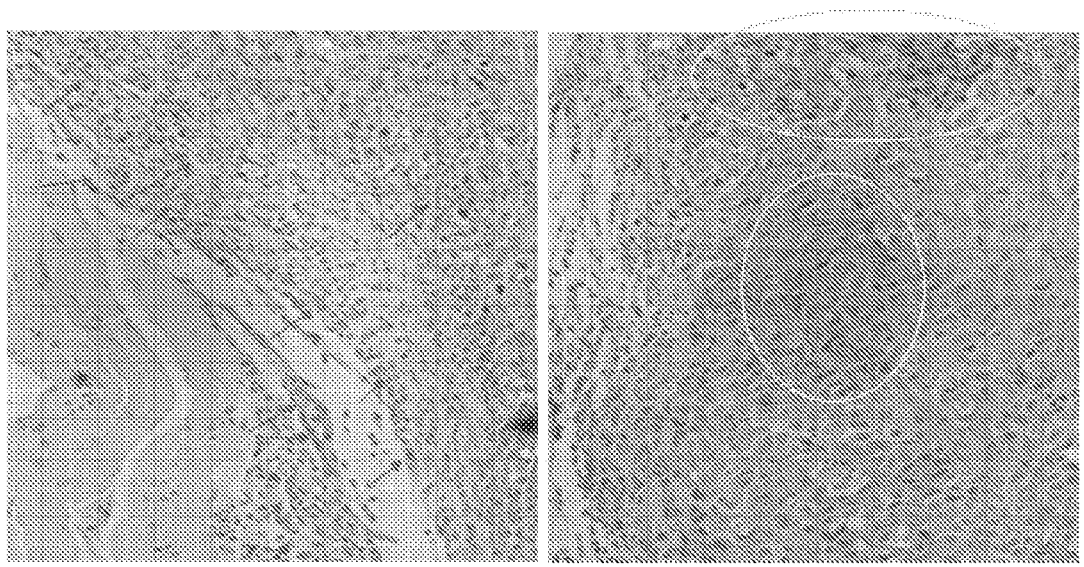
FIG. 27 shows histological sections of tumours removed from nude mice following 6 weeks of treatment.

FIG. 27 shows histological sections of tumours removed from nude mice following 6 weeks of treatment. Sections are stained with H&E the pictures are representative of the tumour. In the control groups larger numbers of blood vessels were visible (red arrows) and fewer areas of necrotic cells. Within the treatment groups there were fewer blood vessels and large areas of pre-necrotic cells represented by yellow circles above.

The invention claimed is:

1. An isolated antibody or antigen binding fragment thereof that specifically binds to receptor activity modifying protein-3 (RAMP-3), wherein the antibody comprises a heavy chain variable region comprising the complementarity determining regions (CDRs) of a heavy chain variable region comprising the amino acid sequence of SEQ ID NO: 2 and a light chain variable region comprising the CDRs of a light chain variable region comprising the amino acid sequence of SEQ ID NO: 10.

2. The antibody or antigen binding fragment of claim 1, wherein the antibody specifically binds to the extracellular domain of RAMP-3.

3. The antibody or antigen binding fragment of claim 1, wherein the antibody is of IgG, IgA or IgM isotype.

4. The antibody or antigen binding fragment of claim 1, wherein the antibody comprises a heavy chain variable region comprising SEQ ID NO: 2 and a light chain variable region comprising SEQ ID NO: 10.

5. The antibody or antigen binding fragment of claim 1, wherein the antibody comprises a heavy chain variable region comprising an amino acid sequence that is at least 95% identical to SEQ ID NO: 2 and a light chain variable region comprising an amino acid sequence that is at least 95% identical to SEQ ID NO: 10.

6. The antibody or antigen binding fragment of claim 1, wherein the antibody comprises a heavy chain variable region comprising an amino acid sequence that is at least 98% identical to SEQ ID NO: 2 and a light chain variable region comprising an amino acid sequence that is at least 98% identical to SEQ ID NO: 10.

7. The antibody or antigen binding fragment of claim 1, which is detectably labeled.

8. The antibody or antigen binding fragment of claim 1, which is conjugated to a diagnostic imaging agent.

9. The antibody or antigen binding fragment of claim 1, which is functionally labeled with a chemotherapeutic or cytotoxic agent.

10. The antibody or antigen binding fragment of claim 9, wherein the chemotherapeutic or cytotoxic agent is a toxin, enzyme, radiolabel, or calicheamicin.

11. A composition comprising the antibody or antigen binding fragment of claim 1 and a pharmaceutically acceptable excipient, diluent, carrier, buffer or stabilizer.

12. The composition of claim 1, further comprising an active agent.

13. The composition of claim 1, wherein the active agent is a chemotherapeutic agent, a cytotoxic agent, or a pain relief drug.

14. An isolated nucleic acid encoding an antibody or antigen binding fragment thereof that specifically binds to receptor activity modifying protein-3 (RAMP-3), wherein the antibody comprises a heavy chain variable region comprising the complementarity determining regions (CDRs) of a heavy chain variable region comprising the amino acid sequence of SEQ ID NO: 2 and a light chain variable region comprising the CDRs of a light chain variable region comprising the amino acid sequence of SEQ ID NO: 10.

15. A vector comprising the nucleic acid molecule of claim 14.

16. An isolated host cell comprising the vector of claim 15.

17. A method of producing an antibody or antigen binding fragment thereof that specifically binds to receptor activity modifying protein-3 (RAMP-3), wherein the antibody comprises a heavy chain variable region comprising the complementarity determining regions (CDRs) of a heavy chain variable region comprising the amino acid sequence of SEQ ID NO: 2 and a light chain variable region comprising the CDRs of a light chain variable region comprising the amino acid sequence of SEQ ID NO: 10, said method comprising culturing the host cell of claim 16 under conditions suitable for expression of the nucleic acid encoding the antibody or antigen binding fragment thereof and isolating the antibody or antigen binding fragment thereof produced by the host cell.

* * * * *

UNITED STATES PATENT AND TRADEMARK OFFICE
CERTIFICATE OF CORRECTION

PATENT NO. : 8,389,237 B2  Page 1 of 1
APPLICATION NO. : 12/597269
DATED : March 5, 2013
INVENTOR(S) : Skerry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 109 days.

Signed and Sealed this
First Day of September, 2015

Michelle K. Lee
*Director of the United States Patent and Trademark Office*

SEQUENCE LISTING

```
<160> NUMBER OF SEQ ID NOS: 70

<210> SEQ ID NO 1
<211> LENGTH: 445
<212> TYPE: DNA
<213> ORGANISM: Mus musculus

<400> SEQUENCE: 1
actagtcgac atgagggccc ctgctcagtt ttttgggatc ttgttgctct tgtttccagg      60
taccagatgt gacatccaga tgacccagtc tccatcctcc ttatctgcct ctctgggaga    120
aagagtcagt ctcacttgtc gggcaagtca ggacattggt agtaacttaa actggcttca    180
gcaggaacca gatggaacta ttaaacgcct gatctacgcc acatccagtt tagattctgg    240
tgtccccaaa aggttcagtg gcagtaggtc tgggtcagat tattctctca ccatcagcag    300
ccttgagtct gaagattttg tagactatta ctgtctacaa tatgctagtt ctcctccgac    360
```

```
gttcggtgga ggcaccaagc tggaaatcaa acgggctgat gctgcaccaa ctgtatccat      420
cttcccacca tccagtaagc ttggg                                            445

<210> SEQ ID NO 2
<211> LENGTH: 159
<212> TYPE: PRT
<213> ORGANISM: Mus musculus

<400> SEQUENCE: 2

Met Val Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Lys Ser Leu Arg Leu Ser Cys Ala Ala Ser Gly Phe Thr Phe
        35                  40                  45

Ser Ser Tyr Gly Met Tyr Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Asn Cys Ala Lys Glu Met Arg Tyr Gly Ser Gly Arg Lys Ala Ile
        115                 120                 125

Lys Tyr Tyr Tyr Gly Met Asp Val Trp Gly Gln Gly Thr Thr Val Thr
    130                 135                 140

Val Ser Ser Ala Ser Thr Lys Gly Pro Ser Val Phe Pro Leu Ala
145                 150                 155

<210> SEQ ID NO 3
<211> LENGTH: 468
<212> TYPE: DNA
<213> ORGANISM: Mus musculus

<400> SEQUENCE: 3
actagtcgac atgaacttcg ggttcagatt ggttttccta gccctcattt taaaaggtgt      60
ccagtgtgaa gtgcagctgg tggagtctgg gggaggctta gtgaagcctg agggtccct     120 gaaactctcc tgtgcagcct ctggattcac tttcagtagt tatgccatgt cttgggttcg     180
ccagactccg gagaagaggc tggagtgggt cgcaaccatt agtagtggtg gtagttacac     240
ctactatcca gacagtgtga agggtcgatt caccatctcc agagacaatg ccaagaacac     300
cctgtacctg caaatgagca gtctgaggtc tgaggacacg gccatgtatt acagtgcaag     360
acataggtac gacgtgaagt ttttgggcta ctggggccaa ggcaccactc tcacagtctc     420
ctcagagagt cagtccttcc caaatgtctt ccccctcgta agcttggg                  468

<210> SEQ ID NO 4
<211> LENGTH: 155
<212> TYPE: PRT
<213> ORGANISM: Mus musculus

<400> SEQUENCE: 4

Leu Val Asp Met Asn Phe Gly Leu Arg Leu Val Phe Leu Ala Leu Ile
1               5                   10                  15

Leu Lys Gly Val Gln Cys Glu Val Gln Leu Val Glu Ser Gly Gly Gly
            20                  25                  30
```

Leu Val Lys Pro Gly Gly Ser Leu Lys Leu Ser Cys Ala Ala Ser Gly
                35                  40                  45

Phe Thr Phe Ser Ser Tyr Ala Met Ser Trp Val Arg Gln Thr Pro Glu
     50                  55                  60

Lys Arg Leu Glu Trp Val Ala Thr Ile Ser Gly Gly Ser Tyr Thr
 65                  70                  75                  80

Tyr Tyr Pro Asp Ser Val Lys Gly Arg Phe Thr Ile Ser Arg Asp Asn
                 85                  90                  95

Ala Lys Asn Thr Leu Tyr Leu Gln Met Ser Ser Leu Arg Ser Glu Asp
             100                 105                 110

Thr Ala Met Tyr Tyr Ser Ala Arg His Arg Tyr Asp Val Lys Phe Leu
         115                 120                 125

Gly Tyr Trp Gly Gln Gly Thr Thr Leu Thr Val Ser Glu Ser Gln
    130                 135                 140

Ser Phe Pro Asn Val Phe Pro Leu Val Ser Leu
145                 150                 155

<210> SEQ ID NO 5
<211> LENGTH: 368
<212> TYPE: DNA
<213> ORGANISM: Mus musculus

<400> SEQUENCE: 5
aggtgaagct gcaggagtca ggggcagagc ttgtgaggtc aggggcccca gtcaagttgt      60
cctgcacagc ttctggcttc aacattaaag actactatat gcactgggtg aagcagaggc     120
ctgaacaggg cctggagtgg attggatgga ttgatcctga aatggtgat actgaatatg      180 ccccgaattt ccagggcaag gccactatga ctgcagacac atcctccaac acagcctacc     240
tgcagctcag cagcctgaca tctgaggaca ctgccgtcta ttactgtaat gcccatgttt     300
tattactacg gggagtagag gatgctatgg actactgggg ccaagggacc acggtcaccg     360
tctcctca                                                             368

<210> SEQ ID NO 6
<211> LENGTH: 122
<212> TYPE: PRT
<213> ORGANISM: Mus musculus

<400> SEQUENCE: 6

Val Lys Leu Gln Glu Ser Gly Ala Glu Leu Val Arg Ser Gly Ala Pro
 1               5                  10                  15

Val Lys Leu Ser Cys Thr Ala Ser Gly Phe Asn Ile Lys Asp Tyr Tyr
             20                  25                  30

Met His Trp Val Lys Gln Arg Pro Glu Gln Gly Leu Glu Trp Ile Gly
         35                  40                  45

Trp Ile Asp Pro Glu Asn Gly Asp Thr Glu Tyr Ala Pro Asn Phe Gln
    50                  55                  60

Gly Lys Ala Thr Met Thr Ala Asp Thr Ser Ser Asn Thr Ala Tyr Leu
 65                  70                  75                  80

Gln Leu Ser Ser Leu Thr Ser Glu Asp Thr Ala Val Tyr Tyr Cys Asn
                 85                  90                  95

Ala His Val Leu Leu Leu Arg Gly Val Glu Asp Ala Met Asp Tyr Trp
             100                 105                 110

Gly Gln Gly Thr Thr Val Thr Val Ser Ser
         115                 120

<210> SEQ ID NO 7
<211> LENGTH: 472
<212> TYPE: DNA
<213> ORGANISM: Mus musculus

<400> SEQUENCE: 7

```
atggacttcg ggttgagctg ggttttcctt gttgctattt taaaaggtgt ccaatgtgag      60
gtgcagctgg tggagtctgg gggaggcttg gtacagccag gcggtccct gagactctcc     120 tgtacagctt ctagattcac gtttgctgat tatgctatca cctgggtccg ccaggctcca    180
gggaaggggc tggagtgggt aggtttcatt agaagcaaac cttttggtgg acagcagca    240 tacgccgcgt ctgtgaaagg cagattcacc atctcaagag atgattccaa aagcatcgcc   300
tatctgcaat tgaaccgcct gaaaaccgaa gacacagccg tgtattactg tagtagagcc   360
cctttatcga gtgactacag tcctccttga cgtctgggg gccaagggac cacggtcacc    420
gtctcctcaa gatccgcctc caccaagggc ccatccgtct tccccctggc ac            472
```

<210> SEQ ID NO 8
<211> LENGTH: 157
<212> TYPE: PRT
<213> ORGANISM: Mus musculus

<400> SEQUENCE: 8

```
Met Asp Phe Gly Leu Ser Trp Val Phe Leu Val Ala Ile Leu Lys Gly
 1               5                  10                  15

Val Gln Cys Glu Val Gln Leu Val Glu Ser Gly Gly Gly Leu Val Gln
            20                  25                  30

Pro Gly Arg Ser Leu Arg Leu Ser Cys Thr Ala Ser Arg Phe Thr Phe
        35                  40                  45

Ala Asp Tyr Ala Ile Thr Trp Val Arg Gln Ala Pro Gly Lys Gly Leu
    50                  55                  60

Glu Trp Val Gly Phe Ile Arg Ser Lys Pro Phe Gly Gly Thr Ala Ala
65                  70                  75                  80

Tyr Ala Ala Ser Val Lys Gly Arg Phe Thr Ile Ser Arg Asp Asp Ser
                85                  90                  95

Lys Ser Ile Ala Tyr Leu Gln Leu Asn Arg Leu Lys Thr Glu Asp Thr
            100                 105                 110

Ala Val Tyr Tyr Cys Ser Arg Ala Pro Leu Ser Ser Asp Tyr Ser Pro
        115                 120                 125

Ser Leu Asp Val Trp Gly Gln Gly Thr Thr Val Thr Val Ser Ser Arg
    130                 135                 140

Ser Ala Ser Thr Lys Gly Pro Ser Val Phe Pro Leu Ala
145                 150                 155
```

<210> SEQ ID NO 9
<211> LENGTH: 426
<212> TYPE: DNA
<213> ORGANISM: Mus musculus

<400> SEQUENCE: 9

```
atgagggccc ctgctcagtt ttttgggatc ttgttgctct tgtttccagg taccagatgt      60
gacatccaga tgacccagtc tccatcctcc ttatctgcct ctctgggaga aagagtcagt    120
ctcacttgtc gggcaagtca ggacattggt agtaacttaa actggcttca gcaggaacca    180
gatggaacta ttaaacgcct gatctacgcc acatccagtt tagattctgg tgtcccaaa    240 aggttcagtg gcagtaggtc tgggtcagat tattctctca ccatcagcag ccttgagtct    300
gaagattttg tagactatta ctgtctacaa tatgctagtt ctcctccgac gttcggtgga    360
```

```
ggcaccaagc tggaaatcaa acgggctgat gctgcaccaa ctgtatccat cttcccacca    420
tccagt                                                              426
```

<210> SEQ ID NO 10
<211> LENGTH: 145
<212> TYPE: PRT
<213> ORGANISM: Mus musculus

<400> SEQUENCE: 10

```
Met Arg Ala Pro Ala Gln Phe Phe Gly Ile Leu Leu Leu Leu Phe Pro
1               5                   10                  15

Gly Thr Arg Cys Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Ser Asn Leu Asn Trp Leu Gln Gln Glu Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ala
            100                 105                 110

Ser Ser Pro Pro Thr Phe Gly Gly Gly Thr Lys Leu Glu Ile Lys Arg
        115                 120                 125

Ala Asp Ala Ala Pro Thr Val Ser Ile Phe Pro Pro Ser Ser Lys Leu
    130                 135                 140

Gly
145
```

<210> SEQ ID NO 11
<211> LENGTH: 324
<212> TYPE: DNA
<213> ORGANISM: Mus musculus

<400> SEQUENCE: 11

```
gacatccaga tgacgcagtc tccagcctcc ctatctgcat ctgtgggaga aactgtcacc    60
atcacatgtc gagcaagtga gaatatttac agttatttag catggtatca gcagaaacag   120
ggaaaatctc ctcagctcct ggtctataat gcaaaaacct tagcagaagg tgtgccatca   180
aggttcagtg gcagtggatc aggcacacag ttttctctga agatcaacag cctgcagcct   240
gaagattttg ggagttatta ctgtcaacat cattatggta ctcctccgac gttcggtgga   300
ggcaccaagc tggaaatcaa acgg                                          324
```

<210> SEQ ID NO 12
<211> LENGTH: 108
<212> TYPE: PRT
<213> ORGANISM: Mus musculus

<400> SEQUENCE: 12

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45
```

```
Tyr Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Pro
                85                  90                  95

Thr Phe Gly Gly Gly Thr Lys Leu Glu Ile Lys Arg
            100                 105

<210> SEQ ID NO 13
<211> LENGTH: 516
<212> TYPE: DNA
<213> ORGANISM: Mus musculus

<400> SEQUENCE: 13 tttttttgaat tccaccatga agttgcctgt taggctgttg gtgctgatgt tctggattcc    60
tgcttccagc agtgatgttg tgatgaccca aactccactc tccctgcctg tcagtcttgg   120
agatcaagcc tccatctctt gcagatctag tcagagcctt gtacacagta atggaaacac   180
ctatttacat tggtacctgc agaagccagg ccagtctcca aagctcctga tctacaaagt   240
ttccaaccga ttttctgggg tcccagacag gttcagtggc agtggatcag ggacagattt   300
cacactcaag atcagcagag tggaggctga ggatctggga gtttatttct gctctcaaag   360
tacacatgtt ccattcacgt tcggctcggg gacaaagttg gaaataaaac gggctgatgc   420
tgcaccaact gtatccatct tcccaccatc cagtgagcag ttaacatctg gaggtgcctc   480
agtcgtgtgc ttcttgaaca acttctaccc caaaga                             516

<210> SEQ ID NO 14
<211> LENGTH: 171
<212> TYPE: PRT
<213> ORGANISM: Mus musculus

<400> SEQUENCE: 14

Phe Leu Asn Ser Thr Met Lys Leu Pro Val Arg Leu Leu Val Leu Met
  1               5                  10                  15

Phe Trp Ile Pro Ala Ser Ser Asp Val Val Met Thr Gln Thr Pro
            20                  25                  30

Leu Ser Leu Pro Val Ser Leu Gly Asp Gln Ala Ser Ile Ser Cys Arg
            35                  40                  45

Ser Ser Gln Ser Leu Val His Ser Asn Gly Asn Thr Tyr Leu His Trp
 50                  55                  60

Tyr Leu Gln Lys Pro Gly Gln Ser Pro Lys Leu Leu Ile Tyr Lys Val
 65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Phe Cys Ser Gln Ser Thr His Val Pro Phe Thr Phe Gly
            115                 120                 125

Ser Gly Thr Lys Leu Glu Ile Lys Arg Ala Asp Ala Ala Pro Thr Val
130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys
                165                 170
```

<210> SEQ ID NO 15
<211> LENGTH: 484
<212> TYPE: DNA
<213> ORGANISM: Mus musculus

<400> SEQUENCE: 15

| | | | | | |
|---|---|---|---|---|---|
| atggagacag | acacactcct | gctatgggta | ctgctgctct | gggttccagg | ttccactggt | 60 |
| gacattgtgc | tgacacagtc | tcctgcttcc | ttagctgtat | ctctgggca | gagggccacc | 120 |
| atctcgtaca | gggccagcaa | agtgtcagt | acatctggct | atagttatat | gcactggaac | 180 |
| caacagaaac | caggacagcc | acccagactc | ctcatctatc | ttgtatccaa | cctagaatct | 240 |
| ggggtccctg | ccaggttcag | tggcagtggg | tctgggacag | acttcaccct | caacatccat | 300 |
| cctgtggagg | aggaggatgc | tgcaacctat | tactgtcagc | acattaggga | gcttacacgt | 360 |
| tcggaggggg | gcaccaagct | ggaaatcaaa | cggagatctc | gaactgtggc | tgcaccatct | 420 |
| gtcttcatct | tcccgccatc | tgatgagcag | ttgaaatctg | gaactgcctc | tgttgtgtgc | 480 |
| ctgc | | | | | | 484 |

<210> SEQ ID NO 16
<211> LENGTH: 161
<212> TYPE: PRT
<213> ORGANISM: Mus musculus

<400> SEQUENCE: 16

Met Glu Thr Asp Thr Leu Leu Trp Val Leu Leu Trp Val Pro
1               5                   10                  15
Gly Ser Thr Gly Asp Ile Val Leu Thr Gln Ser Pro Ala Ser Leu Ala
                20                  25                  30
Val Ser Leu Gly Gln Arg Ala Thr Ile Ser Tyr Arg Ala Ser Lys Ser
        35                  40                  45
Val Ser Thr Ser Gly Tyr Ser Tyr Met His Trp Asn Gln Gln Lys Pro
    50                  55                  60
Gly Gln Pro Pro Arg Leu Leu Ile Tyr Leu Val Ser Asn Leu Glu Ser
65                  70                  75                  80
Gly Val Pro Ala Arg Phe Ser Gly Ser Gly Ser Gly Thr Asp Phe Thr
                85                  90                  95
Leu Asn Ile His Pro Val Glu Glu Asp Ala Ala Thr Tyr Tyr Cys
            100                 105                 110
Gln His Ile Arg Glu Leu Thr Arg Ser Glu Gly Gly Thr Lys Leu Glu
        115                 120                 125
Ile Lys Arg Arg Ser Arg Thr Val Ala Ala Pro Ser Val Phe Ile Phe
    130                 135                 140
Pro Pro Ser Asp Glu Gln Leu Lys Ser Gly Thr Ala Ser Val Val Cys
145                 150                 155                 160
Leu

<210> SEQ ID NO 17
<211> LENGTH: 159
<212> TYPE: PRT
<213> ORGANISM: Mus musculus

<400> SEQUENCE: 17

Met Val Phe Gly Leu Ser Trp Val Phe Leu Val Ala Leu Leu Arg Gly
1               5                   10                  15
Val Gln Cys Gln Val Gln Leu Val Glu Ser Gly Gly Gly Val Val Gln
                20                  25                  30
Pro Gly Lys Ser Leu Arg Leu Ser Cys Ala Ala Ser Gly Phe Thr Phe

```
                        35                  40                  45
Ser Ser Tyr Gly Met Tyr Trp Val Arg Gln Ala Pro Gly Lys Gly Leu
 50                      55                  60

Glu Trp Val Ala Val Ile Ser Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Asn Cys Ala Lys Glu Met Arg Tyr Gly Ser Gly Arg Lys Ala Ile
         115                 120                 125

Lys Tyr Tyr Tyr Gly Met Asp Val Trp Gly Gln Gly Thr Thr Val Thr
     130                 135                 140

Val Ser Ser Ala Ser Thr Lys Gly Pro Ser Val Phe Pro Leu Ala
145                 150                 155

<210> SEQ ID NO 18
<211> LENGTH: 159
<212> TYPE: PRT
<213> ORGANISM: Mus musculus

<400> SEQUENCE: 18

Met Val Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
             20                  25                  30

Pro Gly Lys Ser Leu Arg Leu Ser Cys Ala Ala Ser Gly Phe Thr Phe
         35                  40                  45

Ser Ser Tyr Gly Met Tyr Trp Val Arg Gln Ala Pro Gly Lys Gly Leu
 50                      55                  60

Glu Trp Val Ala Val Ile Ser Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Asn Cys Ala Lys Glu Met Arg Tyr Gly Ser Gly Arg Lys Ala Ile
         115                 120                 125

Lys Tyr Tyr Tyr Gly Met Asp Val Trp Gly Gln Gly Thr Thr Val Thr
     130                 135                 140

Val Ser Pro Ala Ser Thr Lys Gly Pro Ser Val Phe Pro Leu Ala
145                 150                 155

<210> SEQ ID NO 19
<211> LENGTH: 155
<212> TYPE: PRT
<213> ORGANISM: Mus musculus

<400> SEQUENCE: 19

Leu Val Asp Met Asn Phe Gly Phe Ser Leu Val Phe Leu Ala Leu Ile
 1               5                  10                  15

Leu Lys Gly Val Gln Cys Glu Val Gln Leu Val Glu Ser Gly Gly Gly
             20                  25                  30

Leu Val Lys Pro Gly Gly Ser Leu Lys Leu Ser Cys Ala Ala Ser Gly
         35                  40                  45

Phe Thr Phe Ser Ser Tyr Ala Met Ser Trp Val Arg Gln Thr Pro Glu
     50                  55                  60
```

Lys Arg Leu Glu Trp Val Ala Thr Ile Ser Ser Gly Gly Ser Tyr Thr
65                  70                  75                  80

Tyr Tyr Pro Asp Ser Val Lys Gly Arg Phe Thr Ile Ser Arg Asp Asn
                85                  90                  95

Ala Lys Asn Thr Leu Tyr Leu Gln Met Ser Ser Leu Arg Ser Glu Asp
            100                 105                 110

Thr Ala Met Tyr Tyr Ser Ala Arg His Arg Tyr Asp Val Lys Phe Leu
        115                 120                 125

Gly Tyr Trp Gly Gln Gly Thr Thr Leu Thr Val Ser Ser Glu Ser Gln
    130                 135                 140

Ser Phe Pro Asn Val Phe Pro Leu Val Ser Leu
145                 150                 155

<210> SEQ ID NO 20
<211> LENGTH: 155
<212> TYPE: PRT
<213> ORGANISM: Mus musculus

<400> SEQUENCE: 20

Leu Val Asp Met Asn Phe Gly Phe Arg Leu Val Phe Leu Ala Leu Ile
1               5                   10                  15

Leu Lys Gly Val Gln Cys Glu Val Gln Leu Val Glu Ser Gly Gly Gly
            20                  25                  30

Leu Val Lys Pro Gly Gly Ser Leu Lys Leu Ser Cys Ala Ala Ser Gly
        35                  40                  45

Phe Thr Phe Ser Ser Tyr Ala Met Ser Trp Val Arg Gln Thr Pro Glu
    50                  55                  60

Lys Arg Leu Glu Trp Val Ala Thr Ile Ser Ser Gly Gly Ser Tyr Thr
65                  70                  75                  80

Tyr Tyr Pro Asp Ser Val Lys Gly Arg Phe Thr Ile Ser Arg Asp Asn
                85                  90                  95

Ala Lys Asn Thr Leu Tyr Leu Gln Met Ser Ser Leu Arg Ser Glu Asp
            100                 105                 110

Thr Ala Met Tyr Tyr Ser Ala Arg His Arg Tyr Asp Val Lys Phe Leu
        115                 120                 125

Gly Tyr Trp Gly Gln Gly Thr Thr Leu Thr Val Ser Ser Glu Ser Gln
    130                 135                 140

Ser Phe Pro Asn Val Phe Pro Leu Val Ser Leu
145                 150                 155

<210> SEQ ID NO 21
<211> LENGTH: 155
<212> TYPE: PRT
<213> ORGANISM: Mus musculus

<400> SEQUENCE: 21

Leu Val Asp Met Asn Phe Gly Phe Arg Leu Val Phe Leu Ala Leu Ile
1               5                   10                  15

Leu Lys Gly Val Gln Cys Glu Val Gln Leu Val Glu Ser Gly Gly Gly
            20                  25                  30

Leu Val Lys Pro Gly Gly Ser Leu Lys Leu Ser Cys Ala Ala Ser Gly
        35                  40                  45

Phe Thr Phe Ser Ser Tyr Ala Met Ser Trp Val Arg Gln Thr Pro Glu
    50                  55                  60

Lys Arg Leu Glu Trp Val Ala Thr Ile Ser Ser Gly Gly Ser Tyr Thr
65                  70                  75                  80

```
Tyr Tyr Pro Asp Ser Val Lys Gly Arg Phe Thr Ile Ser Arg Asp Asn
                85                  90                  95

Ala Lys Asn Thr Leu Tyr Leu Gln Met Ser Ser Leu Arg Ser Glu Asp
            100                 105                 110

Thr Ala Met Tyr Tyr Ser Ala Arg His Arg Tyr Asp Val Lys Phe Leu
        115                 120                 125

Gly Tyr Trp Gly Gln Gly Thr Thr Leu Thr Val Ser Ser Glu Ser Gln
    130                 135                 140

Ser Phe Pro Asn Val Phe Pro Leu Val Ser Leu
145                 150                 155

<210> SEQ ID NO 22
<211> LENGTH: 155
<212> TYPE: PRT
<213> ORGANISM: Mus musculus

<400> SEQUENCE: 22

Leu Val Asp Met Asn Phe Gly Leu Arg Leu Val Phe Leu Ala Leu Ile
1               5                   10                  15

Leu Lys Gly Val Gln Cys Glu Val Gln Leu Val Glu Ser Gly Gly Gly
            20                  25                  30

Leu Val Lys Pro Gly Gly Ser Leu Lys Leu Ser Cys Ala Ala Ser Gly
        35                  40                  45

Phe Thr Phe Ser Ser Tyr Ala Met Ser Trp Val Arg Gln Thr Pro Glu
    50                  55                  60

Lys Arg Leu Glu Trp Val Val Thr Ile Ser Ser Gly Gly Ser Tyr Thr
65                  70                  75                  80

Tyr Tyr Pro Asp Ser Val Lys Gly Arg Phe Thr Ile Ser Arg Asp Asn
                85                  90                  95

Ala Lys Asn Thr Leu Tyr Leu Gln Met Ser Ser Leu Arg Ser Glu Asp
            100                 105                 110

Thr Ala Met Tyr Tyr Ser Ala Arg His Arg Tyr Asp Val Lys Phe Leu
        115                 120                 125

Gly Tyr Trp Gly Gln Gly Thr Thr Leu Thr Val Ser Ser Glu Ser Gln
    130                 135                 140

Ser Phe Pro Asn Val Phe Pro Leu Val Ser Leu
145                 150                 155

<210> SEQ ID NO 23
<211> LENGTH: 155
<212> TYPE: PRT
<213> ORGANISM: Mus musculus

<400> SEQUENCE: 23

Leu Val Asp Met Asn Phe Gly Leu Arg Leu Val Phe Leu Ala Leu Ile
1               5                   10                  15

Leu Lys Gly Val Gln Cys Glu Val Gln Leu Val Glu Ser Gly Gly Gly
            20                  25                  30

Leu Val Lys Pro Gly Gly Ser Leu Lys Leu Ser Cys Ala Ala Ser Gly
        35                  40                  45

Phe Thr Phe Ser Ser Tyr Ala Met Ser Trp Val Arg Gln Thr Pro Glu
    50                  55                  60

Lys Arg Leu Glu Trp Val Ala Thr Ile Ser Ser Gly Gly Ser Tyr Thr
65                  70                  75                  80

Tyr Tyr Pro Asp Ser Val Lys Gly Arg Phe Thr Ile Ser Arg Asp Asn
                85                  90                  95

Ala Lys Asn Thr Leu Tyr Leu Gln Met Ser Ser Leu Arg Ser Glu Asp
            100                 105                 110
```

```
                    100                 105                 110
Thr Ala Met Tyr Tyr Ser Ala Arg His Arg Tyr Asp Val Lys Phe Leu
            115                 120                 125
Gly Tyr Trp Gly Gln Gly Thr Thr Leu Thr Val Ser Ser Glu Ser Gln
            130                 135                 140
Ser Phe Pro Asn Val Phe Pro Leu Val Ser Leu
145                 150                 155
```

<210> SEQ ID NO 24
<211> LENGTH: 155
<212> TYPE: PRT
<213> ORGANISM: Mus musculus

<400> SEQUENCE: 24

```
Leu Val Asp Met Asn Phe Gly Leu Ser Leu Val Phe Leu Ala Leu Ile
1               5                   10                  15
Leu Lys Gly Val Gln Cys Glu Val Gln Leu Val Glu Ser Gly Gly Gly
            20                  25                  30
Leu Val Lys Pro Gly Gly Ser Leu Lys Leu Ser Cys Ala Ala Ser Gly
            35                  40                  45
Phe Thr Phe Ser Ser Tyr Ala Met Ser Trp Val Arg Gln Thr Pro Glu
50                  55                  60
Lys Arg Leu Glu Trp Val Ala Thr Ile Ser Ser Gly Gly Ser Tyr Thr
65                  70                  75                  80
Tyr Tyr Pro Asp Ser Val Lys Gly Arg Phe Thr Ile Ser Arg Asp Asn
                85                  90                  95
Ala Lys Asn Thr Leu Tyr Leu Gln Met Ser Ser Leu Arg Ser Glu Asp
            100                 105                 110
Thr Ala Met Tyr Tyr Ser Ala Arg His Arg Tyr Asp Val Lys Phe Leu
            115                 120                 125
Gly Tyr Trp Gly Gln Gly Thr Thr Leu Thr Val Ser Ser Glu Ser Gln
            130                 135                 140
Ser Phe Pro Asn Val Phe Pro Leu Val Ser Leu
145                 150                 155
```

<210> SEQ ID NO 25
<211> LENGTH: 121
<212> TYPE: PRT
<213> ORGANISM: Mus musculus

<400> SEQUENCE: 25

```
Val Lys Leu Gln Glu Ser Gly Ala Glu Leu Val Arg Ser Gly Ala Pro
1               5                   10                  15
Val Glu Leu Ser Cys Thr Ala Ser Gly Phe Asn Ile Lys Asp Tyr Tyr
            20                  25                  30
Met His Trp Val Lys Gln Arg Pro Glu Gln Gly Leu Glu Trp Ile Gly
            35                  40                  45
Trp Ile Asp Pro Glu Asn Gly Asp Thr Glu Tyr Ala Pro Asn Phe Gln
50                  55                  60
Gly Lys Ala Thr Met Thr Ala Asp Thr Ser Asn Thr Ala Tyr Leu
65                  70                  75                  80
Gln Leu Ser Ser Leu Thr Ser Glu Asp Thr Ala Val Tyr Tyr Cys Asn
85                  90                  95
Ala His Val Leu Leu Leu Arg Gly Val Glu Asp Ala Met Asp Tyr Trp
                100                 105                 110
Gly Gln Gly Thr Thr Val Pro Ser Pro
            115                 120
```

<210> SEQ ID NO 26
<211> LENGTH: 122
<212> TYPE: PRT
<213> ORGANISM: Mus musculus

<400> SEQUENCE: 26

Gly Gln Ala Gln Glu Ser Gly Ala Glu Leu Val Arg Ser Gly Ala Pro
1               5                   10                  15

Val Lys Leu Ser Cys Thr Ala Ser Gly Phe Asn Ile Lys Asp Tyr Tyr
            20                  25                  30

Met His Trp Val Lys Gln Arg Pro Glu Gln Gly Leu Glu Trp Ile Gly
        35                  40                  45

Trp Ile Asp Pro Glu Asn Gly Asp Thr Glu Tyr Ala Pro Asn Phe Gln
    50                  55                  60

Gly Lys Ala Thr Met Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Asn
                85                  90                  95

Ala His Val Leu Leu Leu Arg Gly Val Glu Asp Ala Met Asp Tyr Trp
            100                 105                 110

Gly Gln Gly Thr Thr Val Thr Val Ser Ser
        115                 120

<210> SEQ ID NO 27
<211> LENGTH: 121
<212> TYPE: PRT
<213> ORGANISM: Mus musculus

<400> SEQUENCE: 27

Val Lys Leu Gln Glu Ser Gly Ala Gly Leu Val Arg Ser Gly Ala Pro
1               5                   10                  15

Val Lys Leu Ser Cys Thr Ala Ser Gly Phe Asn Ile Lys Asp Tyr Tyr
            20                  25                  30

Met His Trp Val Lys Gln Arg Pro Glu Gln Gly Leu Glu Trp Ile Gly
        35                  40                  45

Trp Ile Asp Pro Glu Asn Gly Asp Thr Glu Tyr Ala Pro Asn Phe Gln
    50                  55                  60

Gly Lys Ala Thr Met Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Asn
                85                  90                  95

Ala His Val Leu Leu Leu Arg Gly Val Glu Asp Ala Met Asp Tyr Trp
            100                 105                 110

Gly Gln Gly Thr Thr Val Thr Ser Pro
        115                 120

<210> SEQ ID NO 28
<211> LENGTH: 122
<212> TYPE: PRT
<213> ORGANISM: Mus musculus

<400> SEQUENCE: 28

Val Lys Leu Gln Glu Ser Gly Ala Glu Leu Val Arg Ser Gly Ala Pro
1               5                   10                  15

Val Lys Leu Ser Cys Thr Ala Ser Gly Phe Asn Ile Lys Asp Tyr Tyr
            20                  25                  30

Met His Trp Val Lys Gln Arg Pro Glu Gln Gly Leu Glu Trp Ile Gly

```
                35                  40                  45
Trp Ile Asp Pro Glu Asn Gly Asp Thr Glu Tyr Ala Pro Asn Phe Gln
 50                  55                  60

Gly Lys Ala Thr Met Thr Ala Asp Thr Ser Ser Asn Thr Ala Tyr Leu
 65                  70                  75                  80

Gln Leu Ser Ser Leu Thr Ser Glu Asp Thr Ala Val Tyr Tyr Cys Asn
                 85                  90                  95

Ala His Val Leu Leu Leu Arg Gly Val Glu Asp Ala Met Asp Tyr Trp
                100                 105                 110

Gly Gln Gly Thr Thr Val Thr Val Ser Ser
            115                 120

<210> SEQ ID NO 29
<211> LENGTH: 121
<212> TYPE: PRT
<213> ORGANISM: Mus musculus

<400> SEQUENCE: 29

Val Lys Leu Gln Glu Ser Arg Ala Glu Leu Val Arg Ser Gly Ala Pro
 1               5                  10                  15

Val Lys Leu Ser Cys Thr Ala Ser Gly Phe Asn Ile Lys Asp Tyr Tyr
                 20                  25                  30

Met His Trp Val Lys Gln Arg Pro Glu Gln Gly Leu Glu Trp Ile Gly
             35                  40                  45

Trp Ile Asp Pro Glu Asn Gly Asp Thr Glu Tyr Ala Pro Asn Phe Gln
 50                  55                  60

Gly Lys Ala Thr Met Thr Ala Asp Thr Ser Ser Asn Thr Ala Tyr Leu
 65                  70                  75                  80

Gln Leu Ser Ser Leu Thr Ser Glu Asp Thr Ala Val Tyr Tyr Cys Asn
                 85                  90                  95

Ala His Val Leu Leu Leu Arg Gly Val Glu Asp Ala Met Asp Tyr Trp
                100                 105                 110

Gly Gln Gly Thr Thr Val Thr Ser Pro
            115                 120

<210> SEQ ID NO 30
<211> LENGTH: 122
<212> TYPE: PRT
<213> ORGANISM: Mus musculus

<400> SEQUENCE: 30

Val Gln Leu Gln Glu Ser Gly Ala Glu Leu Val Arg Ser Gly Ala Pro
 1               5                  10                  15

Val Lys Leu Ser Cys Thr Ala Ser Gly Phe Asn Ile Lys Asp Tyr Tyr
                 20                  25                  30

Met His Trp Val Lys Gln Arg Pro Glu Gln Gly Leu Glu Trp Ile Gly
             35                  40                  45

Trp Ile Asp Pro Glu Asn Gly Asp Thr Glu Tyr Ala Pro Asn Phe Gln
 50                  55                  60

Gly Lys Ala Thr Met Thr Ala Asp Thr Ser Ser Asn Thr Ala Tyr Leu
 65                  70                  75                  80

Gln Leu Ser Ser Leu Thr Ser Glu Asp Thr Ala Val Tyr Tyr Cys Asn
                 85                  90                  95

Ala His Val Leu Leu Leu Arg Gly Val Glu Asp Ala Met Asp Tyr Trp
                100                 105                 110

Gly Gln Gly Thr Thr Val Thr Val Ser Ser
            115                 120
```

<210> SEQ ID NO 31
<211> LENGTH: 122
<212> TYPE: PRT
<213> ORGANISM: Mus musculus

<400> SEQUENCE: 31

Val Lys Leu Gln Glu Ser Gly Ala Glu Leu Val Arg Ser Gly Ala Pro
1               5                   10                  15

Val Lys Leu Ser Cys Thr Ala Ser Gly Phe Asn Ile Lys Asp Tyr Tyr
            20                  25                  30

Met His Trp Val Lys Gln Arg Pro Glu Gln Gly Leu Glu Trp Ile Gly
        35                  40                  45

Trp Ile Asp Pro Glu Asn Gly Asp Thr Glu Tyr Ala Pro Asn Phe Gln
    50                  55                  60

Gly Lys Ala Thr Met Thr Ala Asp Thr Ser Ser Asn Thr Ala Tyr Leu
65                  70                  75                  80

Gln Leu Ser Ser Leu Thr Ser Glu Asp Thr Ala Val Tyr Tyr Cys Asn
                85                  90                  95

Ala His Val Leu Leu Arg Gly Val Glu Asp Ala Met Asp Tyr Trp
            100                 105                 110

Gly Gln Gly Thr Thr Val Thr Val Ser Ser
        115                 120

<210> SEQ ID NO 32
<211> LENGTH: 157
<212> TYPE: PRT
<213> ORGANISM: Mus musculus

<400> SEQUENCE: 32

Met Asp Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Pro
            20                  25                  30

Pro Gly Arg Ser Leu Arg Leu Ser Cys Thr Ala Ser Arg Phe Thr Phe
        35                  40                  45

Ala Asp Tyr Ala Ile Thr Trp Val Arg Gln Ala Pro Gly Lys Gly Leu
    50                  55                  60

Glu Trp Val Gly Phe Ile Arg Ser Lys Pro Phe Gly Gly Thr Ala Ala
65                  70                  75                  80

Tyr Ala Ala Ser Val Lys Gly Arg Phe Thr Ile Ser Arg Asp Asp Ser
                85                  90                  95

Lys Ser Ile Ala Tyr Leu Gln Leu Asn Arg Leu Lys Thr Glu Asp Thr
            100                 105                 110

Ala Val Tyr Tyr Cys Ser Arg Ala Pro Leu Ser Ser Asp Tyr Ser Pro
        115                 120                 125

Ser Leu Asp Val Trp Gly Gln Gly Thr Thr Val Thr Val Ser Ser Arg
    130                 135                 140

Ser Ala Ser Thr Lys Gly Pro Ser Val Phe Pro Leu Ala
145                 150                 155

<210> SEQ ID NO 33
<211> LENGTH: 157
<212> TYPE: PRT
<213> ORGANISM: Mus musculus

<400> SEQUENCE: 33

Met Asp Phe Gly Leu Ser Trp Val Phe Leu Val Ala Ile Leu Lys Gly

```
                1               5              10              15
Val Gln Cys Glu Val Gln Leu Val Glu Ser Gly Gly Gly Leu Val Gln
                20                      25                      30

Pro Gly Arg Ser Leu Arg Leu Ser Cys Thr Ala Ser Arg Phe Thr Phe
                35                      40                      45

Ala Asp Tyr Ala Ile Thr Trp Val Arg Gln Ala Pro Gly Lys Gly Leu
        50                      55                      60

Glu Trp Val Gly Phe Ile Arg Ser Lys Pro Phe Gly Gly Thr Ala Ala
65                      70                      75                      80

Tyr Ala Ala Ser Val Lys Gly Arg Phe Thr Ile Ser Arg Asp Asp Ser
                        85                      90                      95

Lys Ser Ile Ala Tyr Leu Gln Leu Asn Arg Leu Lys Thr Glu Asp Thr
                        100                     105                     110

Ala Val Tyr Tyr Cys Ser Arg Ala Pro Leu Ser Ser Asp Tyr Ser Pro
                        115                     120                     125

Ser Leu Asp Val Trp Gly Gln Gly Thr Thr Val Thr Val Ser Ser Arg
                130                     135                     140

Ser Ala Ser Thr Lys Gly Pro Ser Val Phe Pro Leu Ala
145                     150                     155
```

<210> SEQ ID NO 34
<211> LENGTH: 157
<212> TYPE: PRT
<213> ORGANISM: Mus musculus
<220> FEATURE:
<221> NAME/KEY: misc_feature
<222> LOCATION: (83)..(83)
<223> OTHER INFORMATION: Xaa can be any naturally occurring amino acid

<400> SEQUENCE: 34

```
Met Asp Phe Gly Leu Ser Trp Val Phe Leu Val Ala Ile Leu Lys Gly
1               5                       10                      15

Val Gln Cys Glu Val Gln Leu Val Glu Ser Gly Gly Gly Leu Val Gln
                20                      25                      30

Pro Gly Arg Ser Leu Arg Leu Ser Cys Thr Ala Ser Arg Phe Thr Phe
                35                      40                      45

Ala Asp Tyr Ala Ile Thr Trp Val Arg Gln Ala Pro Gly Lys Gly Leu
        50                      55                      60

Glu Trp Val Gly Phe Ile Arg Ser Lys Pro Phe Gly Gly Thr Ala Ala
65                      70                      75                      80

Tyr Ala Xaa Ser Val Lys Gly Arg Phe Thr Ile Ser Arg Asp Asp Ser
                        85                      90                      95

Lys Ser Ile Ala Tyr Leu Gln Leu Asn Arg Leu Lys Thr Glu Asp Thr
                        100                     105                     110

Ala Val Tyr Tyr Cys Ser Arg Ala Pro Leu Ser Ser Asp Tyr Ser Pro
                        115                     120                     125

Ser Leu Asp Val Trp Gly Gln Gly Thr Thr Val Thr Val Ser Ser Arg
                130                     135                     140

Ser Ala Ser Thr Lys Gly Pro Ser Val Phe Pro Leu Ala
145                     150                     155
```

<210> SEQ ID NO 35
<211> LENGTH: 157
<212> TYPE: PRT
<213> ORGANISM: Mus musculus

<400> SEQUENCE: 35

Met Asp Phe Gly Leu Ser Leu Val Phe Leu Val Ala Ile Leu Lys Gly

```
                1               5                  10                  15
Val Gln Cys Glu Val Gln Leu Val Glu Ser Gly Gly Gly Leu Val Gln
                20                  25                  30

Pro Gly Arg Ser Leu Arg Leu Ser Cys Thr Ala Ser Arg Phe Thr Phe
            35                  40                  45

Ala Asp Tyr Ala Ile Thr Trp Val Arg Gln Ala Pro Gly Lys Gly Leu
    50                  55                  60

Glu Trp Val Gly Phe Ile Arg Ser Lys Pro Phe Gly Gly Thr Ala Ala
65                  70                  75                  80

Tyr Ala Ala Ser Val Lys Gly Arg Phe Thr Ile Ser Arg Asp Asp Ser
                85                  90                  95

Lys Ser Ile Ala Tyr Leu Gln Leu Asn Arg Leu Lys Thr Glu Asp Thr
                100                 105                 110

Ala Val Tyr Tyr Cys Ser Arg Ala Pro Leu Ser Ser Asp Tyr Ser Pro
                115                 120                 125

Ser Leu Asp Val Trp Gly Gln Gly Thr Thr Val Thr Val Ser Ser Arg
            130                 135                 140

Ser Ala Ser Thr Lys Gly Pro Ser Val Phe Pro Leu Ala
145                 150                 155

<210> SEQ ID NO 36
<211> LENGTH: 151
<212> TYPE: PRT
<213> ORGANISM: Mus musculus

<400> SEQUENCE: 36

Met Asp Phe Gly Leu Ser Trp Val Phe Leu Val Ala Ile Leu Lys Gly
1               5                   10                  15

Val Gln Cys Glu Val Gln Leu Val Glu Ser Gly Gly Gly Leu Val Gln
                20                  25                  30

Pro Gly Arg Ser Leu Gly Leu Ser Cys Thr Ala Ser Arg Phe Thr Phe
            35                  40                  45

Ala Asp Tyr Ala Ile Thr Trp Val Arg Gln Ala Pro Gly Lys Gly Leu
    50                  55                  60

Glu Trp Val Gly Phe Ile Arg Ser Lys Pro Phe Gly Gly Thr Ala Ala
65                  70                  75                  80

Tyr Ala Ala Ser Val Lys Gly Arg Phe Thr Ile Ser Arg Asp Asp Ser
                85                  90                  95

Lys Ser Ile Ala Tyr Leu Gln Leu Asn Arg Leu Lys Thr Glu Asp Thr
                100                 105                 110

Ala Val Tyr Tyr Cys Ser Arg Ala Pro Leu Ser Ser Asp Tyr Ser Pro
                115                 120                 125

Ser Leu Asp Val Trp Gly Gln Gly Thr Thr Val Thr Val Ser Ser Arg
            130                 135                 140

Ser Ala Ser Thr Lys Gly Pro
145                 150

<210> SEQ ID NO 37
<211> LENGTH: 148
<212> TYPE: PRT
<213> ORGANISM: Mus musculus

<400> SEQUENCE: 37

Leu Val Asp Met Arg Ala Pro Ala Gln Phe Phe Gly Ile Leu Leu Leu
1               5                   10                  15

Leu Phe Pro Gly Thr Arg Cys Asp Ile Gln Met Thr Gln Ser Pro Ser
            20                  25                  30
```

```
Ser Leu Ser Ala Ser Leu Gly Glu Arg Val Ser Leu Thr Cys Arg Ala
        35                  40                  45

Ser Gln Asp Ile Gly Ser Asn Leu Asn Trp Leu Gln Gln Glu Pro Asp
 50                  55                  60

Gly Thr Ile Lys Arg Leu Ile Tyr Ala Thr Ser Ser Leu Asp Ser Gly
 65                  70                  75                  80

Val Pro Lys Arg Phe Ser Gly Ser Arg Ser Gly Ser Asp Tyr Ser Leu
                 85                  90                  95

Thr Ile Ser Ser Leu Glu Ser Glu Asp Phe Val Asp Tyr Tyr Cys Leu
                100                 105                 110

Gln Tyr Ala Ser Ser Pro Pro Thr Phe Gly Gly Gly Thr Lys Leu Glu
            115                 120                 125

Ile Lys Arg Ala Asp Ala Ala Pro Thr Val Ser Ile Phe Pro Pro Ser
        130                 135                 140

Ser Lys Leu Gly
145

<210> SEQ ID NO 38
<211> LENGTH: 148
<212> TYPE: PRT
<213> ORGANISM: Mus musculus

<400> SEQUENCE: 38

Leu Val Asp Met Arg Ala Pro Ala Gln Ile Phe Gly Ile Leu Leu Leu
1               5                  10                  15

Leu Phe Pro Gly Thr Arg Cys Asp Ile Gln Met Thr Gln Ser Pro Ser
                20                  25                  30

Ser Leu Ser Ala Ser Leu Gly Glu Arg Val Ser Leu Thr Cys Arg Ala
        35                  40                  45

Ser Gln Asp Ile Gly Ser Asn Leu Asn Trp Leu Gln Gln Glu Pro Asp
 50                  55                  60

Gly Thr Ile Lys Arg Leu Ile Tyr Ala Thr Ser Ser Leu Asp Ser Gly
 65                  70                  75                  80

Val Pro Lys Arg Phe Ser Gly Ser Arg Ser Gly Ser Asp Tyr Ser Leu
                 85                  90                  95

Thr Ile Ser Ser Leu Glu Ser Glu Asp Phe Val Asp Tyr Tyr Cys Leu
                100                 105                 110

Gln Tyr Ala Ser Ser Pro Pro Thr Phe Gly Gly Gly Thr Lys Leu Glu
            115                 120                 125

Ile Lys Arg Ala Asp Ala Ala Pro Thr Val Ser Ile Phe Pro Pro Ser
        130                 135                 140

Ser Lys Leu Gly
145

<210> SEQ ID NO 39
<211> LENGTH: 148
<212> TYPE: PRT
<213> ORGANISM: Mus musculus

<400> SEQUENCE: 39

Leu Val Asp Met Arg Ala Pro Ala Gln Phe Leu Gly Ile Leu Leu Leu
1               5                  10                  15

Leu Phe Pro Gly Thr Arg Cys Asp Ile Gln Met Thr Gln Ser Pro Ser
                20                  25                  30

Ser Leu Ser Ala Ser Leu Gly Glu Arg Val Ser Leu Thr Cys Arg Ala
        35                  40                  45
```

-continued

Ser Gln Asp Ile Gly Ser Asn Leu Asn Trp Leu Gln Gln Glu Pro Asp
    50                  55                  60

Arg Thr Ile Lys Arg Leu Ile Tyr Ala Thr Ser Ser Asp Ser Gly
65                  70                  75                  80

Val Pro Lys Arg Phe Ser Gly Ser Arg Ser Gly Ser Asp Tyr Ser Leu
                85                  90                  95

Thr Ile Ser Ser Leu Glu Ser Glu Asp Ser Val Asp Tyr Tyr Cys Leu
            100                 105                 110

Gln Tyr Ala Ser Ser Pro Pro Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Lys Leu Gly
145

<210> SEQ ID NO 40
<211> LENGTH: 148
<212> TYPE: PRT
<213> ORGANISM: Mus musculus

<400> SEQUENCE: 40

Leu Val Asp Met Arg Thr Pro Ala Gln Phe Phe Gly Ile Leu Leu Leu
1               5                   10                  15

Leu Phe Pro Gly Thr Arg Cys Asp Ile Gln Met Thr Gln Ser Pro Ser
            20                  25                  30

Ser Leu Ser Ala Ser Leu Gly Glu Arg Val Ser Leu Thr Cys Arg Thr
        35                  40                  45

Ser Gln Asp Ile Gly Ser Asn Leu Asn Trp Leu Gln Gln Glu Pro Asp
    50                  55                  60

Gly Thr Ile Lys Arg Leu Ile Tyr Ala Thr Ser Ser Leu Asp Ser Gly
65                  70                  75                  80

Val Pro Lys Arg Phe Ser Gly Ser Arg Ser Gly Ser Asp Tyr Ser Leu
                85                  90                  95

Thr Ile Ser Ser Leu Glu Ser Glu Asp Phe Val Asp Tyr Tyr Cys Leu
            100                 105                 110

Gln Tyr Ala Ser Ser Pro Pro Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Lys Leu Gly
145

<210> SEQ ID NO 41
<211> LENGTH: 148
<212> TYPE: PRT
<213> ORGANISM: Mus musculus

<400> SEQUENCE: 41

Thr Ser Arg Met Val Ser Thr Pro Gln Phe Leu Gly Phe Leu Leu Leu
1               5                   10                  15

Leu Phe Pro Gly Thr Arg Cys Asp Ile Gln Met Thr Gln Ser Pro Ser
            20                  25                  30

Ser Leu Ser Ala Ser Leu Gly Glu Arg Val Ser Leu Thr Cys Arg Ala
        35                  40                  45

Ser Gln Asp Ile Gly Ser Asn Leu Asn Trp Leu Gln Gln Glu Pro Asp
    50                  55                  60

Gly Thr Ile Lys Arg Leu Ile Tyr Ala Thr Ser Ser Leu Asp Ser Gly

```
                65                  70                  75                  80
Val Pro Lys Arg Phe Ser Gly Ser Arg Ser Gly Ser Asp Tyr Ser Leu
                    85                  90                  95
Thr Ile Ser Ser Leu Glu Ser Glu Asp Phe Val Asp Tyr Tyr Cys Leu
                100                 105                 110
Gln Tyr Ala Ser Ser Pro Pro Thr Phe Gly Gly Gly Thr Lys Leu Glu
                115                 120                 125
Ile Lys Arg Ala Asp Ala Ala Pro Thr Val Ser Ile Phe Pro Pro Ser
            130                 135                 140
Ser Lys Leu Gly
145

<210> SEQ ID NO 42
<211> LENGTH: 108
<212> TYPE: PRT
<213> ORGANISM: Mus musculus

<400> SEQUENCE: 42

Asp Ile Gln Met Thr Gln Ser Pro Ala Ser Leu Ser Ala Ser Val Gly
1               5                   10                  15
Glu Thr Val Thr Ile Thr Cys Arg Ala Ser Glu Asn Ile Tyr Ser Tyr
                20                  25                  30
Leu Ala Trp Tyr Gln Gln Lys Gln Gly Lys Ser Pro Gln Leu Leu Val
            35                  40                  45
Tyr Asn Ala Lys Thr Leu Ala Glu Gly Val Pro Ser Arg Phe Ser Gly
        50                  55                  60
Ser Gly Ser Gly Thr Gln Phe Ser Leu Lys Ile Asn Ser Leu Gln Pro
65                  70                  75                  80
Glu Asp Phe Gly Ser Tyr Tyr Cys Gln His His Tyr Gly Thr Pro Pro
                85                  90                  95
Thr Phe Gly Gly Gly Thr Lys Leu Glu Ile Lys Arg
                100                 105

<210> SEQ ID NO 43
<211> LENGTH: 107
<212> TYPE: PRT
<213> ORGANISM: Mus musculus

<400> SEQUENCE: 43

Asp Ile Gln Met Thr Gln Ser Pro Ala Ser Leu Ser Ala Ser Val Gly
1               5                   10                  15
Glu Thr Val Thr Ile Thr Cys Arg Ala Ser Glu Asn Ile Tyr Ser Tyr
                20                  25                  30
Leu Ala Trp Tyr Gln Gln Lys Gln Gly Lys Ser Pro Gln Leu Leu Val
            35                  40                  45
Tyr Asn Ala Lys Thr Leu Ala Glu Gly Val Pro Ser Arg Phe Ser Gly
        50                  55                  60
Ser Gly Ser Gly Thr Gln Phe Ser Leu Lys Ile Asn Ser Leu Gln Pro
65                  70                  75                  80
Glu Asp Phe Gly Ser Tyr Tyr Cys Gln His Arg Tyr Gly Thr Pro Pro
                85                  90                  95
Thr Phe Gly Gly Gly Thr Lys Leu Ile Lys Arg
                100                 105

<210> SEQ ID NO 44
<211> LENGTH: 107
<212> TYPE: PRT
<213> ORGANISM: Mus musculus
```

```
<400> SEQUENCE: 44

His Gln Met Thr Gln Ser Pro Ala Ser Leu Ser Ala Ser Val Gly Glu
1               5                   10                  15

Thr Val Thr Ile Thr Cys Arg Ala Ser Glu Asn Ile Tyr Ser Tyr Leu
            20                  25                  30

Ala Trp Tyr Gln Gln Lys Gln Gly Lys Ser Pro Gln Leu Leu Val Tyr
        35                  40                  45

Asn Ala Lys Thr Leu Ala Glu Gly Val Pro Ser Arg Phe Ser Gly Ser
    50                  55                  60

Gly Ser Gly Thr Gln Phe Ser Leu Lys Ile Asn Ser Leu Gln Pro Glu
65                  70                  75                  80

Asp Phe Gly Ser Tyr Tyr Cys Gln His His Tyr Gly Thr Pro Pro Thr
                85                  90                  95

Phe Gly Gly Gly Thr Lys Leu Glu Ile Lys Arg
            100                 105

<210> SEQ ID NO 45
<211> LENGTH: 107
<212> TYPE: PRT
<213> ORGANISM: Mus musculus

<400> SEQUENCE: 45

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
                85                  90                  95

Thr Phe Gly Gly Gly Thr Lys Leu Glu Ile Lys
            100                 105

<210> SEQ ID NO 46
<211> LENGTH: 108
<212> TYPE: PRT
<213> ORGANISM: Mus musculus

<400> SEQUENCE: 46

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
                85                  90                  95

Thr Phe Gly Gly Gly Thr Lys Leu Glu Ile Lys Arg
```

<210> SEQ ID NO 47
<211> LENGTH: 171
<212> TYPE: PRT
<213> ORGANISM: Mus musculus

<400> SEQUENCE: 47

```
Phe Leu Asn Ser Thr Met Lys Leu Pro Val Arg Leu Val Leu Met
1               5                   10                  15

Phe Trp Ile Pro Ala Ser Ser Ser Asp Val Val Met Thr Gln Thr Pro
            20                  25                  30

Leu Ser Leu Pro Val Ser Leu Gly Asp Gln Ala Ser Ile Ser Cys Arg
        35                  40                  45

Ser Ser Gln Ser Leu Val His Ser Asn Gly Asn Thr Tyr Leu His Trp
    50                  55                  60

Tyr Leu Gln Lys Pro Gly Gln Ser Pro Lys Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Phe Cys Ser Gln Ser Thr His Val Pro Phe Thr Phe Gly
        115                 120                 125

Ser Gly Thr Arg Leu Glu Ile Lys Arg Ala Asp Ala Ala Pro Thr Val
    130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys
                165                 170
```

<210> SEQ ID NO 48
<211> LENGTH: 168
<212> TYPE: PRT
<213> ORGANISM: Mus musculus

<400> SEQUENCE: 48

```
Ser Thr Met Lys Leu Pro Val Arg Leu Val Leu Met Phe Trp Ile
1               5                   10                  15

Pro Ala Ser Ser Ser Asp Val Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Ser Asn Gly Asn Thr Tyr Leu His Trp Tyr Leu Gln
    50                  55                  60

Lys Pro Gly Gln Ser Pro Lys Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Phe Thr Phe Gly Ser Gly Thr
        115                 120                 125

Lys Leu Glu Ile Lys Arg Ala Asn Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160
```

Phe Leu Asn Asn Phe Tyr Pro Lys
                165

<210> SEQ ID NO 49
<211> LENGTH: 171
<212> TYPE: PRT
<213> ORGANISM: Mus musculus

<400> SEQUENCE: 49

Phe Leu Asn Ser Thr Met Lys Leu Pro Val Arg Leu Leu Val Leu Met
1               5                   10                  15

Phe Trp Ile Pro Ala Ser Ser Asp Val Val Met Thr Gln Thr Pro
            20                  25                  30

Leu Ser Leu Pro Val Ser Leu Gly Asp Gln Ala Ser Ile Ser Cys Arg
        35                  40                  45

Ser Ser Gln Ser Leu Val His Ser Asn Gly Asn Thr Tyr Leu His Trp
    50                  55                  60

Tyr Leu Gln Lys Pro Gly Gln Ser Pro Lys Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Phe Cys Ser Gln Ser Thr His Val Pro Phe Thr Phe Gly
        115                 120                 125

Ser Gly Thr Lys Leu Glu Ile Lys Arg Ala Asp Ala Ala Pro Thr Val
    130                 135                 140

Ser Ile Phe Pro Pro Ser Ser Glu Gln Leu Thr Ser Gly Gly Ala Ser
145                 150                 155                 160

Val Met Cys Phe Leu Asn Asn Phe Tyr Pro Arg
                165                 170

<210> SEQ ID NO 50
<211> LENGTH: 171
<212> TYPE: PRT
<213> ORGANISM: Mus musculus

<400> SEQUENCE: 50

Phe Leu Asn Ser Thr Met Lys Leu Pro Val Arg Leu Leu Val Leu Met
1               5                   10                  15

Phe Trp Ile Pro Ala Ser Ser Asp Val Val Met Thr Gln Thr Pro
            20                  25                  30

Leu Pro Leu Pro Val Ser Leu Gly Asp Gln Ala Ser Ile Ser Cys Arg
        35                  40                  45

Ser Ser Gln Ser Leu Val His Ser Asn Gly Asn Thr Tyr Leu His Trp
    50                  55                  60

Tyr Leu Gln Lys Pro Gly Gln Ser Pro Lys Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Phe Cys Ser Gln Ser Thr His Val Pro Phe Thr Phe Gly
        115                 120                 125

Ser Gly Thr Lys Leu Glu Ile Lys Arg Ala Asp Ala Ala Pro Thr Val
    130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys
                165                 170

<210> SEQ ID NO 51
<211> LENGTH: 169
<212> TYPE: PRT
<213> ORGANISM: Mus musculus

<400> SEQUENCE: 51

Asn Ser Thr Met Lys Leu Pro Val Arg Leu Val Leu Met Phe Trp
1               5                   10                  15

Ile Pro Ala Ser Ser Asp Val Val Met Thr Gln Thr Pro Leu Ser
                20                  25                  30

Leu Pro Val Ser Leu Gly Asp Gln Ala Ser Ile Ser Cys Arg Ser Ser
            35                  40                  45

Gln Ser Leu Val His Ser Asn Gly Asn Thr Tyr Leu His Trp Tyr Leu
    50                  55                  60

Gln Lys Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Leu Gly Val
                100                 105                 110

Tyr Phe Cys Ser Gln Ser Thr His Val Pro Phe Thr Phe Gly Ser Gly
            115                 120                 125

Thr Lys Leu Glu Ile Lys Arg Ala Asp Ala Ala Pro Thr Val Ser Ile
    130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys
                165

<210> SEQ ID NO 52
<211> LENGTH: 161
<212> TYPE: PRT
<213> ORGANISM: Mus musculus

<400> SEQUENCE: 52

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Tyr Arg Ala Ser Lys Ser
            35                  40                  45

Val Ser Thr Ser Gly Tyr Ser Tyr Met His Trp Asn Gln Gln Lys Pro
    50                  55                  60

Gly His Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Arg His Ile Arg Glu Leu Thr Arg Ser Glu Gly Gly Thr Lys Leu Glu
    115                 120                 125

Ile Lys Arg Arg Ser Arg Thr Val Ala Ala Pro Ser Val Phe Ile Phe

```
                130                 135                 140
Pro Pro Ser Asp Glu Gln Leu Lys Ser Gly Thr Ala Ser Val Val Cys
145                 150                 155                 160

Leu

<210> SEQ ID NO 53
<211> LENGTH: 161
<212> TYPE: PRT
<213> ORGANISM: Mus musculus

<400> SEQUENCE: 53

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Leu Thr Arg Ser Glu Gly Gly Thr Lys Leu Glu
        115                 120                 125

Ile Lys Arg Arg Ser Arg Thr Val Ala Ala Pro Ser Val Leu Ile Phe
    130                 135                 140

Pro Pro Ser Asp Glu Gln Leu Lys Ser Gly Thr Ala Ser Val Val Cys
145                 150                 155                 160

Leu

<210> SEQ ID NO 54
<211> LENGTH: 161
<212> TYPE: PRT
<213> ORGANISM: Mus musculus

<400> SEQUENCE: 54

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Leu Thr Arg Ser Glu Gly Gly Thr Lys Leu Glu
        115                 120                 125

Ile Lys Arg Arg Ser Arg Thr Val Ala Ala Pro Ser Val Phe Ile Phe
```

Pro Pro Ser Asp Glu Gln Leu Lys Ser Gly Thr Ala Ser Val Val Cys
145                 150                 155                 160

Leu

<210> SEQ ID NO 55
<211> LENGTH: 161
<212> TYPE: PRT
<213> ORGANISM: Mus musculus

<400> SEQUENCE: 55

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Leu Thr Arg Ser Glu Gly Gly Thr Lys Leu Glu
        115                 120                 125

Ile Lys Arg Arg Ser Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu

<210> SEQ ID NO 56
<211> LENGTH: 161
<212> TYPE: PRT
<213> ORGANISM: Mus musculus

<400> SEQUENCE: 56

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Leu Thr Arg Ser Glu Gly Gly Thr Lys Leu Glu
        115                 120                 125

Ile Lys Arg Arg Ser Arg Thr Val Ala Ala Pro Ser Val Phe Ile Phe

```
            130                 135                 140
Pro Pro Ser Asp Glu Gln Leu Lys Ser Gly Thr Ala Ser Val Val Cys
145                 150                 155                 160

Leu
```

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
cgagcggact cgactcggca c                                          21

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
cttcctaggg tggcggtggc c                                          21

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gtccgcctcc tccttctgct                                            20

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
aagtggagta acatggttat tgt                                        23

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
agccatggag actggagcgc tgc                                        23

<210> SEQ ID NO 62
<211> LENGTH: 24
<212> TYPE: DNA
<213> ORGANISM: Artificial Sequence
<220> FEATURE:
<223> OTHER INFORMATION: Primer

<400> SEQUENCE: 62
gtggcccagt agctggagat tggc                                       24

```
<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
gcgaattcct gccagaccac cag                                            23

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
gtggatccta ccgggcccgg gaca                                           24

<210> SEQ ID NO 65
<211> LENGTH: 34
<212> TYPE: DNA
<213> ORGANISM: Artificial Sequence
<220> FEATURE:
<223> OTHER INFORMATION: Primer

<400> SEQUENCE: 65
gcgaattcaa tccccacgag gccctggctc agcc                                34

<210> SEQ ID NO 66
<211> LENGTH: 33
<212> TYPE: DNA
<213> ORGANISM: Artificial Sequence
<220> FEATURE:
<223> OTHER INFORMATION: Primer

<400> SEQUENCE: 66
caggatccta caagagtgat gaggaagggg atg                                 33

<210> SEQ ID NO 67
<211> LENGTH: 35
<212> TYPE: DNA
<213> ORGANISM: Artificial Sequence
<220> FEATURE:
<223> OTHER INFORMATION: Primer

<400> SEQUENCE: 67
cagaatttcc agagcaggcc gctgcaacca gacag                               35

<210> SEQ ID NO 68
<211> LENGTH: 35
<212> TYPE: DNA
<213> ORGANISM: Artificial Sequence
<220> FEATURE:
<223> OTHER INFORMATION: Primer

<400> SEQUENCE: 68
gtggatccca ccaccaggcc agccatggcg acagt                               35

<210> SEQ ID NO 69
<211> LENGTH: 60
<212> TYPE: PRT
<213> ORGANISM: Human

<400> SEQUENCE: 69

Gly Cys Pro Arg Ala Gly Gly Cys Asn Glu Thr Gly Met Leu Glu Arg
```

```
                1               5                  10                 15

Leu Pro Leu Cys Gly Lys Ala Phe Ala Asp Met Met Gly Lys Val Asp
                20                  25                  30

Val Trp Lys Trp Cys Asn Leu Ser Glu Phe Ile Val Tyr Tyr Glu Ser
        35                  40                  45

Phe Thr Asn Cys Thr Glu Met Glu Ala Asn Val Val
        50                  55                  60

<210> SEQ ID NO 70
<211> LENGTH: 39
<212> TYPE: PRT
<213> ORGANISM: Human

<400> SEQUENCE: 70

Gly Cys Tyr Trp Pro Asn Pro Leu Ala Gln Gly Phe Ile Thr Gly Ile
1               5                   10                  15

His Arg Gln Phe Phe Ser Asn Cys Thr Val Asp Arg Val His Leu Glu
            20                  25                  30

Asp Pro Pro Asp Glu Val Leu
            35
```